United States Patent
Sims et al.

(10) Patent No.: US 6,913,893 B2
(45) Date of Patent: Jul. 5, 2005

(54) IL-1/TNF-α-ACTIVATED KINASE (ITAK), AND METHODS OF MAKING AND USING THE SAME

(75) Inventors: John E. Sims, Seattle, WA (US); G. Duke Virca, Bellevue, WA (US); Timothy A. Bird, Bainbridge Island, WA (US); Dirk M. Anderson, Seattle, WA (US)

(73) Assignee: Immunex Corporation, Thousand Oaks, CA (US)

(*) Notice: Subject to any disclaimer, the term of this patent is extended or adjusted under 35 U.S.C. 154(b) by 196 days.

(21) Appl. No.: 10/372,736

(22) Filed: Feb. 21, 2003

(65) Prior Publication Data

US 2003/0166223 A1 Sep. 4, 2003

Related U.S. Application Data

(60) Continuation of application No. 09/544,794, filed on Apr. 7, 2000, now Pat. No. 6,541,232, which is a division of application No. 08/870,529, filed on Jun. 6, 1997, now Pat. No. 6,080,557.
(60) Provisional application No. 60/059,979, filed on Jun. 10, 1996.

(51) Int. Cl.$^7$ .................. G01N 33/53; C07K 14/00; C12P 21/06; C12N 5/02
(52) U.S. Cl. .................. 435/7.1; 530/350; 435/69.1; 435/325
(58) Field of Search .................. 435/7.1, 89.1, 435/325; 530/350

(56) References Cited

FOREIGN PATENT DOCUMENTS

| WO | WO 95/33051 | 12/1995 |
|---|---|---|
| WO | WO 98/37094 | 8/1998 |

OTHER PUBLICATIONS

Bird, "Signalling Via IL–1 Receptors," European Vascular Biology Association, Annual Conference 1995, Proceedings.

Callard et al., The Cytokine FactsBook, Academic Press Ltd., 1994, p. 31.

Fujiwara et al., EST, Genbank Accession No. D63222, May 1996.

Guesdon et al., "Interleukin 1 and Tumor Necrosis Factor Stimulate Two Novel Protein Kinases That Phosphorylate the Heat Shock Protein hsp27 and β–Casein," *Journal of Biological Chemistry* 268(6):4236–4243, 1993.

Guesdon et al., "Specific activation of β–casein kinase by the inflammatory cytokines interleukin 1 and tumour necrosis factor," *Biochem. Journal* 304:761–768, 1994.

Guesdon et al., "β–Casein Kinase: Exclusive Acivation By IL–1 or TNF and Substrate Specificity," *Cytokine* 6(5):558, Abstract No. A119, 1994.

Guesdon et al., "Substrate Specificity of the IL1– and TNF–Activated β Casein Kinase," *Cytokine* 7:603, Abstract No. A48, 1995.

Letwin et al., "A mammalian dual specificity protein kinase, Nek1, is related to the NIMA cell cycle regulator and highly expressed in meiotic germ cells," *EMBO Journal* 11(10):3521–3531, 1992.

McLaughlin et al., "Identification of Mitogen–activated Protein (MAP) Kinase–activated Protein Kinase–3, a Novel Substrate of CSBP p38 MAP Kinase," *Journal of Biological Chemistry* 271(14):8488–8492, 1996.

Saklatvala et al., "Interleukin 1 (IL1) and tumour necrosis factor (TNF) signal transduction," *Phil. Trans. R. Soc. Lond. B* 351:151–157, 1996.

*Primary Examiner*—Janet Andres
(74) *Attorney, Agent, or Firm*—Paul B. Tran; Stuart L. Watt; Ron K. Levy

(57) ABSTRACT

Purified and isolated IL-1/TNF-α-activated kinase (ITAK), nucleic acids encoding ITAK, processes for production of recombinant forms of ITAK, pharmaceutical compositions containing ITAK, and use of ITAK in therapies and in various assays, including assays to detect antagonists and agonists of ITAK are provided.

2 Claims, 6 Drawing Sheets

FIGURE 1A

```
TCTTCGCGGG GTTGCTGGGC TGACGGATCC GCGGGCCGGC ATCTGAAGCG AGCGGGACGC    60

AGCGCGGCCA GGGCCTCCGG GCATACGCAG GCTGGTCCCC AAGGCCCGCG GCCGCCGCC    119

ATG TCG GTG CTG GGC GAG TAC GAG CGA CAC TGC GAT TCC ATC AAC TCG    167
Met Ser Val Leu Gly Glu Tyr Glu Arg His Cys Asp Ser Ile Asn Ser
 1               5                  10                  15

GAC TTT GGG AGC GAG TCC GGG GGT TGC GGG GAC TCG AGT CCG GGG CCT    215
Asp Phe Gly Ser Glu Ser Gly Gly Cys Gly Asp Ser Ser Pro Gly Pro
              20                  25                  30

AGC GCC AGT CAG GGG CCG CGA GCC GGC GGC GGC GCG GCG GAG CAG GAG    263
Ser Ala Ser Gln Gly Pro Arg Ala Gly Gly Gly Ala Ala Glu Gln Glu
          35                  40                  45

GAA CTG CAC TAC ATC CCC ATC CGC GTC CTG GGC CGC GGC GCC TTC GGG    311
Glu Leu His Tyr Ile Pro Ile Arg Val Leu Gly Arg Gly Ala Phe Gly
      50                  55                  60

GAA GCC ACG CTG TAC CGC CGC ACC GAG GAT GAC TCA CTG GTT GTG TGG    359
Glu Ala Thr Leu Tyr Arg Arg Thr Glu Asp Asp Ser Leu Val Val Trp
 65                  70                  75                  80

AAG GAA GTC GAT TTG ACC CGG CTG TCT GAG AAG GAA CGT CGT GAT GCC    407
Lys Glu Val Asp Leu Thr Arg Leu Ser Glu Lys Glu Arg Arg Asp Ala
                  85                  90                  95

TTG AAT GAG ATA GTT ATT CTG GCA CTG CTG CAG CAC GAC AAC ATT ATT    455
Leu Asn Glu Ile Val Ile Leu Ala Leu Leu Gln His Asp Asn Ile Ile
              100                 105                 110

GCC TAC TAC AAT CAC TTC ATG GAC AAT ACC ACG CTG CTG ATT GAG CTG    503
Ala Tyr Tyr Asn His Phe Met Asp Asn Thr Thr Leu Leu Ile Glu Leu
          115                 120                 125

GAA TAT TGT AAT GGA GGG AAC CTG TAT GAC AAA ATC CTT CGT CAG AAG    551
Glu Tyr Cys Asn Gly Gly Asn Leu Tyr Asp Lys Ile Leu Arg Gln Lys
      130                 135                 140

GAC AAG TTG TTT GAG GAA GAG ATG GTG GTG TGG TAC CTA TTT CAG ATT    599
Asp Lys Leu Phe Glu Glu Glu Met Val Val Trp Tyr Leu Phe Gln Ile
145                 150                 155                 160

GTT TCA GCA GTG AGC TGC ATC CAT AAA GCT GGA ATC CTT CAT AGA GAT    647
Val Ser Ala Val Ser Cys Ile His Lys Ala Gly Ile Leu His Arg Asp
                  165                 170                 175
```

FIGURE 1B

```
ATA AAG ACA TTA AAT ATT TTT CTG ACC AAG GCA AAC CTG ATA AAA CTT         695
Ile Lys Thr Leu Asn Ile Phe Leu Thr Lys Ala Asn Leu Ile Lys Leu
        180             185             190

GGA GAT TAT GGC CTA GCA AAG AAA CTT AAT TCT GAG TAT TCC ATG GCT         743
Gly Asp Tyr Gly Leu Ala Lys Lys Leu Asn Ser Glu Tyr Ser Met Ala
        195             200             205

GAG ACG CTT GTG GGA ACC CCA TAT TAC ATG TCT CCA GAG CTC TGT CAA         791
Glu Thr Leu Val Gly Thr Pro Tyr Tyr Met Ser Pro Glu Leu Cys Gln
        210             215             220

GGA GTA AAG TAC AAT TTC AAG TCT GAT ATC TGG GCA GTT GGC TGC GTC         839
Gly Val Lys Tyr Asn Phe Lys Ser Asp Ile Trp Ala Val Gly Cys Val
225             230             235             240

ATT TTT GAA CTG CTT ACC TTA AAG AGG ACG TTT GAT GCT ACA AAC CCA         887
Ile Phe Glu Leu Leu Thr Leu Lys Arg Thr Phe Asp Ala Thr Asn Pro
            245             250             255

CTT AAC CTG TGT GTG AAG ATC GTG CAA GGA ATT CGG GCC ATG GAA GTT         935
Leu Asn Leu Cys Val Lys Ile Val Gln Gly Ile Arg Ala Met Glu Val
        260             265             270

GAC TCT AGC CAG TAC TCT TTG GAA TTG ATC CAA ATG GTT CAT TCG TGC         983
Asp Ser Ser Gln Tyr Ser Leu Glu Leu Ile Gln Met Val His Ser Cys
        275             280             285

CTT GAC CAG GAT CCT GAG CAG AGA CCT ACT GCA GAT GAA CTT CTA GAT        1031
Leu Asp Gln Asp Pro Glu Gln Arg Pro Thr Ala Asp Glu Leu Leu Asp
        290             295             300

CGC CCT CTT CTC AGG AAA CGC AGG AGA GAG ATG GAG GAA AAA GTC ACT        1079
Arg Pro Leu Leu Arg Lys Arg Arg Arg Glu Met Glu Glu Lys Val Thr
305             310             315             320

CTG CTT AAT GCA CCT ACA AAG AGA CCA AGG TCA AGC ACT GTG ACT GAA        1127
Leu Leu Asn Ala Pro Thr Lys Arg Pro Arg Ser Ser Thr Val Thr Glu
            325             330             335

GCA CCC ATT GCT GTA GTA ACA TCA CGA ACC AGT GAA GTC TAT GTT TGG        1175
Ala Pro Ile Ala Val Val Thr Ser Arg Thr Ser Glu Val Tyr Val Trp
        340             345             350

GGT GGT GGA AAA TCC ACC CCC CAG AAA CTG GAT GTT ATC AAG AGT GGC        1223
Gly Gly Gly Lys Ser Thr Pro Gln Lys Leu Asp Val Ile Lys Ser Gly
        355             360             365
```

FIGURE 1C

| | | | | | | | | | | | | | | | |
|---|---|---|---|---|---|---|---|---|---|---|---|---|---|---|---|
| TGT | AGT | GCC | CGG | CAG | GTC | TGT | GCA | GGG | AAT | ACC | CAC | TTT | GCT | GTG | GTC | 1271 |
| Cys | Ser | Ala | Arg | Gln | Val | Cys | Ala | Gly | Asn | Thr | His | Phe | Ala | Val | Val | |
| | 370 | | | | 375 | | | | | 380 | | | | | | |

```
TGT AGT GCC CGG CAG GTC TGT GCA GGG AAT ACC CAC TTT GCT GTG GTC      1271
Cys Ser Ala Arg Gln Val Cys Ala Gly Asn Thr His Phe Ala Val Val
    370             375                 380

ACA GTG GAG AAG GAA CTG TAC ACT TGG GTG AAC ATG CAA GGA GGC ACT      1319
Thr Val Glu Lys Glu Leu Tyr Thr Trp Val Asn Met Gln Gly Gly Thr
385             390                 395                     400

AAA CTC CAT GGT CAG CTG GGC CAT GGA GAC AAA GCC TCC TAT CGA CAG      1367
Lys Leu His Gly Gln Leu Gly His Gly Asp Lys Ala Ser Tyr Arg Gln
                405                 410                 415

CCA AAG CAT GTG GAA AAG TTG CAA GGC AAA GCT ATC CAT CAG GTG TCA      1415
Pro Lys His Val Glu Lys Leu Gln Gly Lys Ala Ile His Gln Val Ser
            420                 425                 430

TGT GGT GAT GAT TTC ACT GTC TGT GTG ACT GAT GAG GGT CAG CTC TAT      1463
Cys Gly Asp Asp Phe Thr Val Cys Val Thr Asp Glu Gly Gln Leu Tyr
            435                 440                 445

GCC TTC GGA TCA GAT TAT TAT GGC TGC ATG GGG GTG GAC AAA GTT GCT      1511
Ala Phe Gly Ser Asp Tyr Tyr Gly Cys Met Gly Val Asp Lys Val Ala
    450                 455                 460

GGC CCT GAA GTG CTA GAA CCC ATG CAG CTG AAC TTC TTC CTC AGC AAT      1559
Gly Pro Glu Val Leu Glu Pro Met Gln Leu Asn Phe Phe Leu Ser Asn
465                 470                 475                 480

CCA GTG GAG CAG GTC TCC TGT GGA GAT AAT CAT GTG GTG GTT CTG ACA      1607
Pro Val Glu Gln Val Ser Cys Gly Asp Asn His Val Val Val Leu Thr
                485                 490                 495

CGA AAC AAG GAA GTC TAT TCT TGG GGC TGT GGC GAA TAT GGA CGA CTG      1655
Arg Asn Lys Glu Val Tyr Ser Trp Gly Cys Gly Glu Tyr Gly Arg Leu
            500                 505                 510

GGT TTG GAT TCA GAA GAG GAT TAT TAT ACA CCA CAA AAG GTG GAT GTT      1703
Gly Leu Asp Ser Glu Glu Asp Tyr Tyr Thr Pro Gln Lys Val Asp Val
        515                 520                 525

CCC AAG GCC TTG ATT ATT GTT GCA GTT CAA TGT GGC TGT GAT GGG ACA      1751
Pro Lys Ala Leu Ile Ile Val Ala Val Gln Cys Gly Cys Asp Gly Thr
    530                 535                 540

TTT CTG TTG ACC CAG TCA GGC AAA GTG CTG GCC TGT GGA CTC AAT GAA      1799
Phe Leu Leu Thr Gln Ser Gly Lys Val Leu Ala Cys Gly Leu Asn Glu
545                 550                 555                 560
```

FIGURE 1D

```
TTC AAT AAG CTG GGT CTG AAT CAG TGC ATG TCG GGA ATT ATC AAC CAT          1847
Phe Asn Lys Leu Gly Leu Asn Gln Cys Met Ser Gly Ile Ile Asn His
            565                 570                 575

GAA GCA TAC CAT GAA GTT CCC TAC ACA ACG TCC TTT ACC TTG GCC AAA          1895
Glu Ala Tyr His Glu Val Pro Tyr Thr Thr Ser Phe Thr Leu Ala Lys
            580                 585                 590

CAG TTG TCC TTT TAT AAG ATC CGT ACC ATT GCC CCA GGC AAG ACT CAC          1943
Gln Leu Ser Phe Tyr Lys Ile Arg Thr Ile Ala Pro Gly Lys Thr His
            595                 600                 605

ACA GCT GCT ATT GAT GAG CGA GGC CGG CTG CTG ACC TTT GGC TGC AAC          1991
Thr Ala Ala Ile Asp Glu Arg Gly Arg Leu Leu Thr Phe Gly Cys Asn
            610                 615                 620

AAG TGT GGG CAG CTG GGC GTT GGG AAC TAC AAG AAG CGT CTG GGA ATC          2039
Lys Cys Gly Gln Leu Gly Val Gly Asn Tyr Lys Lys Arg Leu Gly Ile
625                 630                 635                 640

AAC CTG TTG GGG GGA CCC CTT GGT GGG AAG CAA GTG ATC AGG GTC TCC          2087
Asn Leu Leu Gly Gly Pro Leu Gly Gly Lys Gln Val Ile Arg Val Ser
            645                 650                 655

TGC GGT GAT GAG TTT ACC ATT GCT GCC ACT GAT GAT AAT CAC ATT TTT          2135
Cys Gly Asp Glu Phe Thr Ile Ala Ala Thr Asp Asp Asn His Ile Phe
            660                 665                 670

GCC TGG GGC AAT GGT GGT AAT GGC CGC CTG GCA ATG ACC CCC ACA GAG          2183
Ala Trp Gly Asn Gly Gly Asn Gly Arg Leu Ala Met Thr Pro Thr Glu
            675                 680                 685

AGA CCA CAT GGC TCT GAT ATC TGT ACC TCA TGG CCT CGG CCT ATT TTT          2231
Arg Pro His Gly Ser Asp Ile Cys Thr Ser Trp Pro Arg Pro Ile Phe
            690                 695                 700

GGA TCT CTG CAT CAT GTC CCG GAC CTG TCT TGC CGT GGA TGG CAT ACC          2279
Gly Ser Leu His His Val Pro Asp Leu Ser Cys Arg Gly Trp His Thr
705                 710                 715                 720

ATT CTC ATC GTT GAG AAA GTA TTG AAT TCT AAG ACC ATC CGT TCC AAT          2327
Ile Leu Ile Val Glu Lys Val Leu Asn Ser Lys Thr Ile Arg Ser Asn
                725                 730                 735

AGC AGT GGC TTA TCC ATT GGA ACT GTG TTT CAG AGC TCT AGC CCG GGA          2375
Ser Ser Gly Leu Ser Ile Gly Thr Val Phe Gln Ser Ser Ser Pro Gly
            740                 745                 750
```

FIGURE 1E

```
GGA GGC GGC GGG GGC GGC GGT GGT GAA GAA GAG GAC AGT CAG CAG GAA       2423
Gly Gly Gly Gly Gly Gly Gly Gly Glu Glu Glu Asp Ser Gln Gln Glu
        755                 760                 765

TCT GAA ACT CCT GAC CCA AGT GGA GGC TTC CGA GGA ACA ATG GAA GCA       2471
Ser Glu Thr Pro Asp Pro Ser Gly Gly Phe Arg Gly Thr Met Glu Ala
    770                 775                 780

GAC CGA GGA ATG GAA GGT TTA ATC AGT CCC ACA GAG GCC ATG GGG AAC       2519
Asp Arg Gly Met Glu Gly Leu Ile Ser Pro Thr Glu Ala Met Gly Asn
785                 790                 795                 800

AGT AAT GGG GCC AGC AGC TCC TGT CCT GGC TGG CTT CGA AAG GAG CTG       2567
Ser Asn Gly Ala Ser Ser Ser Cys Pro Gly Trp Leu Arg Lys Glu Leu
            805                 810                 815

GAA AAT GCA GAA TTT ATC CCC ATG CCT GAC AGC CCA TCT CCT CTC AGT       2615
Glu Asn Ala Glu Phe Ile Pro Met Pro Asp Ser Pro Ser Pro Leu Ser
        820                 825                 830

GCA GCG TTT TCA GAA TCT GAG AAA GAT ACC CTG CCC TAT GAA GAG CTG       2663
Ala Ala Phe Ser Glu Ser Glu Lys Asp Thr Leu Pro Tyr Glu Glu Leu
        835                 840                 845

CAA GGA CTC AAA GTG GCC TCT GAA GCT CCT TTG GAA CAC AAA CCC CAA       2711
Gln Gly Leu Lys Val Ala Ser Glu Ala Pro Leu Glu His Lys Pro Gln
    850                 855                 860

GTA GAA GCC TCG TCA CCT CGG CTG AAT CCT GCA GTA ACC TGT GCT GGG       2759
Val Glu Ala Ser Ser Pro Arg Leu Asn Pro Ala Val Thr Cys Ala Gly
865                 870                 875                 880

AAG GGA ACA CCA CTG ACT CCT CCT GCG TGT GCG TGC AGC TCT CTG CAG       2807
Lys Gly Thr Pro Leu Thr Pro Pro Ala Cys Ala Cys Ser Ser Leu Gln
            885                 890                 895

GTG GAG GTT GAG AGA TTG CAG GGT CTG GTG TTA AAG TGT CTG GCT GAA       2855
Val Glu Val Glu Arg Leu Gln Gly Leu Val Leu Lys Cys Leu Ala Glu
        900                 905                 910

CAA CAG AAG CTA CAG CAA GAA AAC CTC CAG ATT TTT ACC CAA CTG CAG       2903
Gln Gln Lys Leu Gln Gln Glu Asn Leu Gln Ile Phe Thr Gln Leu Gln
        915                 920                 925

AAG TTG AAC AAG AAA TTA GAA GGA GGG CAG CAG GTG GGG ATG CAT TCC       2951
Lys Leu Asn Lys Lys Leu Glu Gly Gly Gln Gln Val Gly Met His Ser
    930                 935                 940
```

FIGURE 1F

```
AAA GGA ACT CAG ACA GCA AAG GAA GAG ATG GAA ATG GAT CCA AAG CCT        2999
Lys Gly Thr Gln Thr Ala Lys Glu Glu Met Glu Met Asp Pro Lys Pro
945             950             955             960

GAC TTA GAT TCA GAT TCC TGG TGC CTC CTG GGA ACA GAC TCC TGT AGA        3047
Asp Leu Asp Ser Asp Ser Trp Cys Leu Leu Gly Thr Asp Ser Cys Arg
                965             970             975

CCC AGC CTC TAGTCTCCTG AGCCTATAGA GCCCCCAGGA GACTGGGACC                3096
Pro Ser Leu

CAAAGAACTT CACAGCACAC TTACCGAATG CAGAGAGCAG CTTTCCTGGC TTTGTTCACT      3156

TGCAGAAAAG GAGCGCAAGG CAGAGGCTCT GAAGCACTTT CCTTGTACAT TTGGAGAGTG      3216

GCATTGCCTT TTAGATAGGA TTAGGCCGGA TATTTTGCTT TTTACCCT                   3264
```

IL-1/TNF-α-ACTIVATED KINASE (ITAK), AND METHODS OF MAKING AND USING THE SAME

CROSS-REFERENCE TO RELATED APPLICATION

This application is a Continuation of U.S. Ser. No. 09/544,794, filed 7 Apr. 2000, now U.S. Pat. No. 6,541,232, which is a Divisional of U.S. Ser. No. 08/870,529, filed 06 Jun. 1997, now U.S. Pat. No. 6,080,557, which claims domestic priority to U.S. Ser. No. 60/059,979, filed 10 Jun. 1996.

TECHNICAL FIELD

The invention is generally directed toward signal transduction pathways associated with inflammation, and more particularly toward IL-1/TNF-α-activated kinases (ITAK)

BACKGROUND OF THE INVENTION

Interleukin-1 (IL-1) and tumor necrosis factor-α (TNF-α) are two cytokines produced systemically and locally in response to infection, injury or immunological challenge. Based upon studies in which the action of one (or the other) cytokine has been specifically blockaded, or in which purified cytokines have been administered, IL-1 and TNF-α have been implicated in a number of disease processes. For example, IL-1 has been implicated in inflammatory diseases including rheumatoid arthritis and other degenerative joint diseases, inflammatory bowel disease, type I diabetes, psoriasis, Alzheimer's disease, and allergy. Overproduction of TNF-α has likewise been implicated in diseases such as reperfusion injury, rheumatoid arthritis, cardiovascular disease, infectious disease such as HIV infection and HIV-induced neuropathy, allergic/atopic diseases, inflammatory disease/autoimmunity, malignancy, transplant difficulties including organ transplant rejection or graft-versus-host disease, cachexia, and congenital, dermatologic, neurologic, renal, toxicity and metabolic/idiopathic diseases. A particular case where the two cytokines are thought to act synergistically is in the induction of the Systemic Inflammatory Response Syndrome.

Because the consequences of uncontrolled production of IL-1 and TNF-α can be severe, considerable effort has been expended on therapies that would limit the production or activity of one, or preferably both, of the cytokines. The prevailing therapy has been to administer proteins that bind specifically to the circulating cytokines, thus preventing them from interacting with their cellular receptors. Typically these protein-based therapeutics are antibodies or 'soluble' receptors (i.e., recombinant versions of the natural cellular receptors which lack transmembrane and signaling domains). An additional protein-based therapeutic is the IL-1 receptor antagonist protein (IL-1ra), which competes for binding to the same cellular receptors as the agonist forms of IL-1, but does not elicit a cellular signal.

The effectiveness of all three types of protein-based therapy is limited because occupation of even a very small number of IL-1 or TNF-α receptors by IL-1 or TNF-α generates a cellular response (and therefore the harmful effects described above). It is therefore necessary to maintain relatively high levels of anti-cytokine antibody, soluble receptor or antagonist protein in order to drive the equilibrium in favor of complex formation (i.e., to effectively prevent binding of IL-1 or TNF-α to their respective receptors). Another drawback to such protein-based therapeutics is that each therapeutic is selective for only one of the two cytokines. Thus, large doses of a multitude of therapeutics must be administered to a patient in order to attempt to control IL-1 and TNF-α production.

Although the biological effects of TNF-α and IL-1 are quite similar, the structures of the cytokines, and the structure of their receptors, are very different. IL-1 and TNF-α appear to have overlapping biological activities because the binding of each cytokine to its receptor appears to affect similar post-receptor signal transduction pathways. Many details of these pathways are unclear.

For example, although both cytokines activate the transcription factors NF-κB and AP-1, which leads to the regulated transcription of a wide variety of genes, the particular receptor-proximal effector molecules that regulate this process is unclear. Additionally, both cytokines have been reported to cause the activation of sphingomyelinases and phospholipases that generate, respectively, ceramide and arachidonic acid. Both cytokines also activate members of the mitogen-activated protein kinase (MAPK) family including ERK1, ERK2, and the stress-activated kinases JNK-1 and p38. This family of kinases is activated, to varying extent, by a wide range of hormones, growth factors, heavy metals, protein synthetic inhibitors and ultraviolet light and therefore activation of such kinases cannot be considered unique to the IL-1/TNF-α signal transduction pathway.

In addition to items activated by both IL-1 and TNF-α, IL-1 has been reported to specifically activate the IL-1 receptor associated kinase, IRAK, (Cao, Henzel and Gao, *Science* 271:1128 (1996)). The cytoplasmic domains of TNF receptors have also been reported to interact with other signal transduction molecules such as TRAF1 and TRAF2, FADD, MORT and TRADD. Such TNF-α receptor-interacting proteins also appear capable of interacting with an extended receptor family, including those that mediate quite distinct cellular responses such as the T- and B-cell activator CD40 and a mediator of apoptosis, fas. (Tewari and Dixit, *Curr. Opin. Genet. Dev.* 6:39, 1996; Lee et al., *J. Exp. Med.* 183:669, 1996).

While certain cellular responses may be elicited by IL-1, TNF-α, or other mediators, the only known signaling event that appears to be uniquely induced by IL-1 or TNF-α, but no other defined stimulus, is a protein serine/threonine kinase activity that could be detected in vitro by its ability to phosphorylate β-casein. Guesdon et al., *J. Biol. Chem.* 268:4236 (1993); *Biochem. J.* 304:761 (1994). This β-casein kinase activity was induced in fibroblasts and other connective-tissue derived cells by IL-1 and TNF-α but not by 21 other agents tested. The structure of the β-casein kinase was not elucidated in this report.

However, there has gone unmet a need for substances and/or methods that provide either repression or stimulation of intracellular effects of both IL-1 and TNF-α. There has also gone unmet a need for substances and methods that provide interaction(s) with the post-receptor pathway(s) of IL-1 and TNF-α, as well as substances and methods that provide opportunities to detect agonists and/or antagonists to IL-1 or TNF-α, including single compounds that act as an agonist or antagonist to both IL-1 and TNF-α. The present invention provides these and other related advantages.

SUMMARY OF THE INVENTION

The present invention provides nucleic acid and amino acid sequences of protein kinases, preferably human, that interact with at least one post-receptor intracellular pathway of both IL-1 and TNF-α. Such kinases are referred to herein as IL-1/TNF-α-activated kinase (ITAK). Such kinases are induced as enzymatically active kinases capable of phosphorylating specific substrate proteins by treatment of suitable cells with IL-1 or TNF-α. The present invention further provides compositions and methods for the isolation and purification of nucleic acid molecules encoding ITAK. Also disclosed herein are methods for expressing and purifying ITAK, as well as specific assays for the detection of inhibitors or stimulators of ITAK activity, which would have utility as antagonists or agonists of IL-1 and TNF-α.

In addition, the present invention is directed to isolated nucleic acids encoding ITAK and to vectors, including expression vectors, capable of expressing ITAK, preferably from a cDNA encoding ITAK. The present invention includes host cells containing such expression vectors, and processes for producing ITAK by culturing such host cells under conditions conducive to expression of ITAK, and preferably the purification of ITAK, including in industrial quantities. In part due to such purification of ITAK, the invention is also directed to antibodies, preferably monoclonal antibodies, specific for ITAK.

The present invention is also directed to assays utilizing ITAK to screen for potential inhibitors or stimulators of ITAK activity, for example as a means of blocking a signal transduced in response to IL-1 or TNF-α. Further, methods of using ITAK in the design of inhibitors of ITAK activity are also disclosed.

In particular, in one aspect, an isolated nucleic acid molecule encoding an IL-1/TNF-α-activated kinase (ITAK) such as a human ITAK, or variant thereof, is provided. In one embodiment, the isolated nucleic acid molecule comprises the sequence of nucleotides in SEQ ID:NO 1, from nucleotide number 1 to nucleotide number 2940. This isolated nucleic acid molecule encodes a protein having the amino acid sequence of SEQ ID:NO 2. In a related embodiment, nucleic acid molecules encoding ITAK variants are provided, including the Lys81→Ala substituted ITAK variant. Within a related aspect, an isolated ITAK or variant thereof is provided.

Within other related aspects, recombinant vectors, including recombinant expression vectors comprising a promoter operably linked to ITAK-coding sequences are provided. The invention further provides host cells containing any such recombinant vectors.

In still another aspect, the invention provides a nucleic acid probe of at least 15 nucleotides in length which is capable of specifically hybridizing to a nucleic acid sequence encoding an IL-1/TNF-α-activated kinase (ITAK).

Within yet another aspect of the invention, a method of screening for an agent that modulates the kinase activity of an IL-1/TNF-α-activated kinase (ITAK) is provided, comprising: (a) contacting a candidate agent with biologically active ITAK under conditions and for a time sufficient to allow the candidate agent to modulate the kinase activity of the ITAK; and (b) measuring the ability of the candidate agent to modulate the ITAK kinase activity. Within one embodiment, the method further comprises isolating the candidate agent.

Within another aspect of the invention, a method for determining whether a selected agent is an IL-1/TNF-α-activated kinase (ITAK) agonist is provided, comprising: (a) exposing the selected agent to an unstimulated ITAK response pathway under conditions and for a time sufficient to allow a stimulation of the pathway; and (b) detecting stimulation of the response pathway and therefrom determining the presence of an ITAK agonist. Within a related aspect, a method for determining whether a selected agent is an IL-1/TNF-α-activated kinase (ITAK) agonist is provided, comprising: (a) measuring the ITAK kinase activity of an ITAK response pathway; (b) exposing the selected agent to the measured ITAK response pathway; and (c) detecting increased ITAK kinase activity in the response pathway.

Within still another aspect of the invention, a method for determining whether a selected agent is an IL-1/TNF-α-activated kinase (ITAK) antagonist is provided, comprising: (a) exposing the selected agent to an ITAK response pathway in the presence of an ITAK agonist under conditions and for a time sufficient to allow a decrease in stimulation of the pathway; and (b) detecting a decrease in the stimulation of the response pathway relative to the stimulation of the response pathway by the ITAK agonist alone, and therefrom determining the presence of an ITAK antagonist. Utilizing such methods, ITAK agonists and ITAK antagonists are provided.

Within yet another aspect, an ITAK phosphorylation substrate peptide acceptor sequence that is not mammalian β-casein and that can be phosphorylated by isolated ITAK at a rate of at least 40 nmol, preferably at least 80 nmol, even more preferably at least 98 nmol phosphate/mg protein/minute is provided.

Within still other aspects of the invention, a method for detecting IL-1/TNF-α-activated kinase (ITAK) activity is provided, comprising: (a) contacting ITAK with an ITAK phosphorylation substrate peptide acceptor sequence that is not mammalian β-casein in the presence of ATP under conditions and for a time sufficient to allow transfer of a γ-phosphate group from an ATP donor to the ITAK phosphorylation substrate peptide acceptor sequence; and (b) measuring the incorporation of phosphate by the ITAK phosphorylation substrate peptide acceptor sequence. Within one embodiment, the ATP is γ-($^{32}$P)-ATP. In related embodiments of the invention, the ITAK phosphorylation substrate peptide acceptor sequence has the amino acid sequence: Arg-Arg-Arg-His-Leu-Pro-Pro-Leu-Leu-Leu-Gln-Ser-Trp-Met-His-Gln-Pro-His-Gln. (SEQ ID:NO 3)

Within another aspect of the invention, a method for treating an IL-1- or TNF-α-mediated inflammatory disorder is provided, comprising administering to a patient a therapeutically effective amount of an ITAK antagonist. The invention further provides kits for detecting ITAK in a sample, comprising: an ITAK phosphorylation substrate peptide acceptor sequence that is not mammalian β-casein and that can be phosphorylated by isolated ITAK at a rate of at least 40 nmol, preferably at least 80 nmol, even more preferably at least 98 nmol phosphate/mg protein/minute; and a means for measuring phosphate incorporated by the ITAK phosphorylation substrate peptide acceptor sequence.

The invention further provides methods for identifying gene products that associate with ITAK, comprising: (a) introducing nucleic acid sequences encoding an ITAK polypeptide into a first expression vector such that ITAK sequences are expressed as part of a fusion protein comprising a functionally incomplete first portion of a protein that is essential to the viability of a host cell; (b) introducing nucleic acid sequences encoding a plurality of candidate gene products that associate with ITAK into a second expression vector such that any candidate gene products are expressed as part of a fusion protein comprising a second functionally incomplete portion of the protein that is essential to the viability of the host cell; (c) introducing the first and second expression vectors into a host cell under conditions and for a time sufficient such that host cell survival is dependent upon reconstitution of both the first and second functionally incomplete portions of the protein into a functionally complete protein; and (d) identifying surviving host cells, and therefrom determining the nucleic acid sequences encoding candidate gene products that associate with ITAK in the second expression vector.

In one embodiment of this aspect of the invention, the host cell is a yeast host cell. In another embodiment of this aspect of the invention the yeast is yeast strain Y190. In related embodiments, the protein that is essential to the viability of the host cell is the modular yeast transcription factor GAL4. In another related embodiment the functionally incomplete first portion of a protein that is essential to the viability of the host cell comprises the N-terminal 147 amino acids of the modular yeast transcription factor GAL4, while in another embodiment the functionally incomplete second portion comprises the C-terminal 114 amino acids of the modular yeast transcription factor GAL4. Within yet another embodiment, the functionally incomplete first portion of a protein that is essential to the viability of the host cell comprises the DNA binding domain of a modular transcription factor. In a related embodiment, the functionally incomplete second portion of a protein that is essential to the viability of a unicellular host comprises a transcriptional activation domain of a modular transcription factor.

These and other aspects of the present invention will become evident upon reference to the following detailed description and attached drawings. Various references are set forth herein that describe certain procedures or compositions (e.g., plasmids, etc.). All references cited herein are incorporated herein by reference in their entirety.

BRIEF DESCRIPTION OF THE DRAWINGS

FIGS. 1A–1F depict a representative human ITAK nucleotide sequence and corresponding amino acid sequence (SEQ ID:NO 8).

DETAILED DESCRIPTION OF THE INVENTION

As noted above, the present invention provides compositions and methods for the isolation and purification of ITAK proteins, which proteins have kinase activities that are specifically induced by exposure of appropriate cells to IL-1 or TNF-α. Inhibitors of IL-1 signal transduction have clinical utility in treating various inflammatory and immune disorders characterized by over-production or unregulated production of IL-1, such as allergy, rheumatoid arthritis, inflammatory bowel disease, psoriasis, and Alzheimer's disease. Inhibition of TNF-α signaling also has clinical utility in treating conditions characterized by overproduction or unregulated production of TNF-α, such as Systemic Inflammatory Response Syndrome, reperfusion injury, cardiovascular disease, infectious disease such as HIV infection and HIV neuropathy, inflammatory disease/autoimmunity, allergic/atopic diseases, malignancy, transplants including organ transplant rejection or graft-versus-host disease, cachexia, congenital, dermatologic, neurologic, renal, toxicity, and metabolic/idiopathic diseases. The disclosure herein of a cDNA that encodes ITAK provides methods and compositions suitable for the inhibition of IL-1 and/or TNF-α, as well as a variety of other advantages.

Applicants' discovery of ITAK enables, among other things, construction of vectors, including expression vectors, comprising nucleic acid sequences encoding ITAK, host cells containing such vectors (for example via transfection or transformation), the production of ITAK, including industrial amounts of ITAK, and antibodies immunoreactive with ITAK. In addition, understanding of the mechanism by which ITAK functions in IL-1 and TNF-α signaling enables the design of assays to detect inhibitors of IL-1 and/or TNF-α activity.

As used herein, the term "ITAK" refers to a genus of polypeptides having kinase activities that are specifically induced by exposure of ITAK source cells to IL-1 or TNF-α, and that are capable of the phosphorylation of dephosphorylated bovine β-casein, or the phosphorylation of other suitable peptide or polypeptide substrates identified by their structural homology to phosphorylation acceptor sites of bovine β-casein. In general, such activities are not induced by PMA, 10% fetal calf serum, PDGF, bradykinin, EGF, TGF-β1, bFGF, interferon-β, interferon-β, histamine, prostaglandin $E_2$, forskolin, A23187, 44° C. heat shock or sodium arsenite (Guesdon et al., *Biochem. J.* 304:761 (1994)). Unless otherwise stated, ITAK also refers to variants and derivatives thereof. In a preferred embodiment, ITAK includes proteins having the amino acid sequence 1–979 of SEQ ID:NO 2, as well as proteins having a high degree of sequence homology (typically at least 90% sequence identity, preferably at least 95% identity, and more preferably at least 98% identity) with such amino acid sequences. ITAK also includes the gene products of the nucleotides 1–2940 of SEQ ID:NO 1 and the amino acid sequences encoded by these nucleotides, as well as the gene products of other ITAK-encoding nucleic acid molecules. Such proteins and/or gene products are preferably biologically active. Full length ITAK has a molecular weight of approximately 110–125 kD as determined by SDS-polyacrylamide gel electrophoresis (SDS-PAGE). ITAK also includes the nucleic acid molecules encoding ITAK.

An "ITAK variant" as used herein refers to a polypeptide substantially homologous to native ITAK, but which has an amino acid sequence different from that of native ITAK (human, rabbit, murine or other mammalian species) because of one or more naturally or non-naturally occurring deletions, insertions or substitutions. The variant amino acid sequence preferably is at least about 80% identical to a native ITAK amino acid sequence, more preferably at least about 90% identical, and further preferably at least about 95% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

One class of ITAK variants is based on the tendency of protein kinases to contain a lysine residue in catalytic subdomain II that is advantageous for maximal enzymatic activity. In particular, mutation of this lysine residue (corresponding to position 81 in the ITAK disclosed in SEQ ID:NO 2) leads to loss of catalytic function in protein kinases. Thus, such a mutant (preferably recombinant) kinase can exert a "dominant negative" phenotype when overexpressed in cells, thereby preventing signalling through the biochemical pathway in which the wild-type ITAK normally functions. Such a variant, for example ITAK A81 in which alanine is substituted for lysine-81, can be particularly advantageous for therapeutic uses in the inhibition of the IL-1 or TNF-α signalling, as discussed further below. Other ITAK variants that lack the protein kinase activity of ITAK, such as ITAK variants having amino acid substitutions other than the Lys→Ala substitution of ITAK A81 and including amino acid deletions, insertions, or substitutions, are encompassed within ITAK variants of the invention.

ITAK variants can comprise conservatively substituted sequences, meaning that a given amino acid residue is replaced by a residue having similar physicochemical characteristics. Examples of conservative substitutions include substitution of one aliphatic residue for another, such as Ile, Val, Leu, or Ala for one another, or substitutions of one polar residue for another, such as between Lys and Arg, Glu and Asp, or Gln and Asn. Other such conservative substitutions, for example, substitutions of entire regions having similar hydrophobicity characteristics, are well known. Naturally occurring ITAK variants are also encompassed by the invention. Examples of such variants are proteins that have amino acid substitutions, result from alternate mRNA splicing events, or result from proteolytic cleavage of the ITAK protein, wherein the proteolytic fragments retain the biological activity of ITAK. Variations attributable to proteolysis include, for example, differences in the N- or C-termini of naturally-occurring ITAK as isolated from cells or tissues, or similar variations detectable upon expression in different types of host cells, due to proteolytic removal of one or more terminal amino acids from the ITAK protein (generally from 1–5 terminal amino acids).

A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Maniatis et al., *Molecular Cloning: A Laboratory Manual*, Cold Spring Harbor Laboratory, 1982, and Sambrook et al., *Molecular Cloning: A Laboratory Manual*, 2nd Ed., Cold Spring Harbor Laboratory, Cold Spring Harbor, N.Y. (1989)). Such sequences are preferably provided in the form of an open reading frame uninterrupted by internal non-translated sequences, or introns, that are typically present in eukaryotic genes. Sequences of non-translated DNA may be present 5' or 3' from an open reading frame, where the same do not interfere with manipulation or expression of the coding region.

The term "isolated" as used herein means an ITAK protein that has been separated from a source cell, whether recombinant or non-recombinant, such that the ITAK protein comprises at least about 90% of the protein content of the composition based on the staining pattern of the composition by sodium dodecyl sulfate-polyacrylamide gel electrophoresis (SDS-PAGE) using the stain Coomassie blue. Typically, the purified protein comprises at least about 92% of the protein content, preferably at least about 94% of the protein content, further preferably at least about 96% of the protein content, and even more preferably at least about 98% of the protein content. In alternative embodiments, no other (undesired) protein is detected pursuant to SDS-PAGE analysis followed by Coomassie blue staining, and preferably no other (undesired) protein is detected pursuant to SDS-PAGE analysis followed by silver staining. An "isolated" nucleic acid molecule means a nucleic acid molecule that encodes ITAK, as discussed further herein, and that has been isolated from its source cell. Additionally, an ITAK gene (or fragment thereof, or variant, etc., also as discussed herein) is considered isolated if it has been separated from its biological source cell nucleic acid molecule, such as a chromosome. Such an isolated gene can be contained within a recombinant nucleic acid molecule.

The term "biologically active" as used herein to refer to ITAK, means ITAK that is capable of phosphorylating a dephosphorylated bovine β-casein, or of phosphorylating synthetic peptide substrates (such as ITAK phosphorylation substrate peptide acceptor sequences provided by the invention) having substantial similarity to one or more of the phosphorylation acceptor sites of bovine β-casein. One such substrate is the polypeptide RRRHLPPLLLQSWMHQPHQ (SEQ ID:NO 3). Preferred conditions for phosphorylating a dephosphorylated bovine β-casein can be found in Guesdon et al., *J. Biol. Chem.* 268:4236 (1993); Guesdon et al., *Biochem. J.* 304:761 (1994), while preferred conditions for the phosphorylation of a synthetic polypeptide RRRHLPPLLLQSWMHQPHQ (SEQ ID:NO 3) can be found in Example 1. In vitro phosphorylation of substrate peptides by ITAK may be adapted to high-throughput screens, for example, by scintillation proximity assays (SPA). Thus, means for measuring phosphate incorporated via ITAK into β-casein or into ITAK phosphorylation substrate peptide acceptor sequences include detection of incorporated $^{32}$P; SPA detection methods known in the art; fluorometric, colorimetric, or spectrophotometric measurements; immunochemical detection, for example by use of antibodies specifically reactive with phosphorylated amino acids or peptides; or related detection methods known to those skilled in the art.

An isolated ITAK according to the invention may be produced by recombinant expression systems as described below or may be produced from naturally occurring cells. ITAK can also be substantially purified, as indicated by a series of phosphoproteins that migrate as 110 kD to 125 kD components in SDS-polyacrylamide gel electrophoresis (SDS-PAGE), and that have identical amino acid sequences as indicated by peptide maps and partial sequence analysis. One process for producing ITAK comprises culturing a host cell transformed with an expression vector comprising a DNA sequence that encodes ITAK under conditions sufficient to promote expression of ITAK. ITAK is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify ITAK. Some or all of the foregoing purification steps, in various combinations, are well known and can be employed to provide an isolated and purified recombinant protein.

In addition to recombinantly producing ITAK, ITAK may be isolated and purified from any one of the following cell lines: C122 (Sims et al., *Proc. Nat. Acad. Sci. USA* 86:8946–8950, 1989), HUT102 (ATCC TIB162), KB (ATCC CCL17), Raji (ATCC CCL86), SK-Hep-1 (ATCC HTB52 and WI-26 (ATCC CCL95.1). Other sources for ITAK may be used, and ITAK may also be found in other types of cells that produce, or respond to IL-1 or TNF-α. Production of ITAK by a candidate cell can be detected, for example, using the assays discussed herein, such as the assays described above in relation to the determination of ITAK biological activity and in Example 1, and/or via appropriate nucleic acid hybridization assays. Once a source cell, or cell line, for ITAK is identified, ITAK may be isolated and purified by first optionally stimulating the source cells with IL-1 or TNF-α. When desired, such stimulation can be done using techniques that are well-known in the art. IL-1 is used preferably at 1–50 ng/ml and TNF-α is used preferably at 20–200 ng/ml. (Guesdon et al. 1993, 1994) The cells are then harvested, washed and cytoplasmic proteins extracted according to conventional procedures.

Partially purified ITAK occurs as a high molecular weight complex of >350 kD that may contain specifically associating species important to the regulation of ITAK activity. ITAK may also be modified to create ITAK derivatives by forming covalent or aggregative conjugates with other chemical moieties, such as glycosyl groups, polyethylene glycol (PEG) groups, lipids, phosphate, acetyl groups and the like. Covalent derivatives of ITAK may be prepared by linking the chemical moieties to functional groups on ITAK amino acid side chains or at the N-terminus or C-terminus of an ITAK polypeptide. Other derivatives of ITAK within the scope of this invention include covalent or aggregative conjugates of ITAK or its fragments with other proteins or polypeptides, such as by synthesis in recombinant culture as N-terminal or C-terminal fusions. For example, the conjugate may comprise a signal or leader polypeptide sequence (e.g., the α-factor leader of *Saccharomyces*) at the N-terminus of an ITAK polypeptide. The signal or leader peptide co-translationally or post-translationally directs transfer of the conjugate from its site of synthesis to a site inside or outside of the cell membrane or cell wall.

It is possible to utilize an affinity column comprising an ITAK-binding protein, for example an ITAK-binding antibody, to affinity-purify expressed ITAK polypeptides. ITAK polypeptides can be removed from an affinity column using conventional techniques, e.g., in a high salt elution buffer and then dialyzed into a lower salt buffer for use or by changing pH or other components depending on the affinity matrix utilized.

Variants and derivatives of native ITAK that retain the desired biological activity may be obtained by mutations of nucleotide sequences coding for native ITAK polypeptides. Alterations of the native amino acid sequence may be accomplished by any of a number of conventional methods.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, Jan. 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect intramolecular disulfide bridges upon renaturation. Other equivalents can be prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Nucleic acid sequences within the scope of the invention include isolated DNA and RNA sequences that hybridize to the native ITAK nucleotide sequences disclosed herein under conditions of moderate or high stringency, and which encode biologically active ITAK, and their complements. As used herein, conditions of moderate stringency, as known to those having ordinary skill in the art, and as defined by Sambrook et al., *Molecular Cloning: A Laboratory Manual*, 2nd Ed. Vol. 1, pp. 1.101–104, Cold Spring Harbor Laboratory Press, (1989), include use of a prewashing solution for the nitrocellulose filters 5× SSC, 0.5% SDS, 1.0 mM EDTA (pH 8.0), hybridization conditions of 50% formamide, 6× SSC at 42° C. (or other similar hybridization solution, or Stark's solution, in 50% formamide at 42° C.), and washing conditions of about 60° C., 0.5× SSC, 0.1% SDS. Conditions of high stringency are defined as hybridization conditions as above, and with washing at 68° C., 0.2× SSC, 0.1% SDS. The skilled artisan will recognize that the temperature, salt concentration, and chaotrope composition of hybridization and wash solutions may be adjusted as necessary according to factors such as the length and nucleotide base composition of the probe.

Due to the known degeneracy of the genetic code wherein more than one codon can encode the same amino acid, a DNA sequence may vary, for instance from that shown in FIG. 1 and still encode an ITAK protein, such as one having the amino acid sequence of SEQ ID:NO 2. Such variant DNA sequences may result from silent mutations (e.g., occurring during PCR amplification), or may be the product of deliberate mutagenesis of a native sequence.

The invention thus includes equivalent isolated nucleic acid sequences encoding biologically active ITAK, including those selected from: (a) nucleic acid molecules derived from the coding region of a native mammalian ITAK gene; (b) nucleic acid molecules selected from the group consisting of nucleotide sequences SEQ ID:NO 1 and SEQ ID:NO 8; (c) nucleic acid molecules capable of hybridization to a nucleic acid molecule of (a) (or their complementary strands) under conditions of moderate stringency and which encode ITAK; and (d) nucleic acid molecules which are degenerate, as a result of the genetic code, with respect to a nucleic acid molecule defined in (a), (b) or (c) and which codes for ITAK. Preferably, the nucleic acid molecule is DNA, and further preferably the ITAK is biologically active. ITAK proteins and gene products encoded by such equivalent nucleic acid sequences are encompassed by the invention.

Nucleic acid molecules that are equivalents to the DNA sequence of FIG. 1, SEQ ID:NO 1 will hybridize under moderately stringent conditions to the double-stranded native DNA sequences that encode polypeptides comprising amino acid sequences of SEQ ID:NO 2. Examples of ITAKs encoded by such DNA, include, but are not limited to, ITAK fragments and ITAK proteins comprising inactivated KEX2 protease processing site(s), or conservative amino acid substitution(s), including those described above. ITAK proteins encoded by DNA derived from other mammalian species, wherein the DNA will specifically hybridize to the complement of the cDNA of FIG. 1 or SEQ ID:NO 1 or SEQ ID:NO 8 are also encompassed.

ITAK polypeptide conjugates can comprise peptides added to ITAK to facilitate purification and identification of ITAK. Such peptides include, for example, poly-His or the antigenic identification peptides described in U.S. Pat. No. 5,011,912 and in Hopp et al., Bio/Technology 6:1204, 1988. ITAK fusion proteins may further comprise immunoglobulin constant region polypeptides added to ITAK to facilitate purification, identification, and localization of ITAK. The constant region polypeptide preferably is fused to the C-terminus of a soluble ITAK. General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990). A gene fusion encoding the ITAK:Fc fusion protein is inserted into an appropriate expression vector. ITAK:Fc fusion proteins are allowed to assemble much like antibody molecules, whereupon interchain disulfide bonds form between Fc polypeptides, yielding divalent ITAK.

Recombinant vectors, including expression vectors, containing a nucleic acid sequence encoding ITAK can be prepared using well known methods. The expression vectors include an ITAK DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the ITAK DNA sequence. Thus, a promoter nucleotide sequence is operably linked to an ITAK DNA sequence if the promoter nucleotide sequence controls the transcription of the ITAK DNA sequence. The ability to replicate in the desired host cells, usually conferred by an origin of replication, and a selection gene by which transformants are identified, may additionally be incorporated into the expression vector.

In addition, sequences encoding appropriate signal peptides that are not naturally associated. with ITAK can be incorporated into expression vectors. For example, a DNA sequence for a signal peptide (secretory leader) may be fused in-frame to the ITAK sequence so that ITAK is initially translated as a fusion protein comprising the signal peptide. A signal peptide that is functional in the intended host cells enhances extracellular secretion of the ITAK polypeptide. The signal peptide may be cleaved from the ITAK polypeptide upon secretion of ITAK from the cell.

Suitable host cells for expression of ITAK polypeptides include prokaryotes, yeast or higher eukaryotic cells. Appropriate cloning and expression vectors for use with bacterial, fungal, yeast, and mammalian cellular hosts are described, for example, in Pouwels et al., *Cloning Vectors: A Laboratory Manual*, Elsevier, N.Y. (1985). Cell-free translation systems could also be employed to produce ITAK polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, an ITAK polypeptide may include an N-terminal methionine residue to facilitate expression of the recombinant polypeptide in the prokaryotic host cell. The N-terminal Met may be cleaved from the expressed recombinant ITAK polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and an ITAK DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

ITAK polypeptides alternatively may be expressed in yeast host cells, preferably from the *Saccharomyces* genus (e.g., *S. cerevisiae*). Other genera of yeast, such as *Pichia, K. lactis* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene* 107:285–195 (1991); and van den Berg et. al., *Bio/Technology* 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of an ITAK polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant ITAK polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10:2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991. The vectors may be derived from retroviruses. In place of the native signal sequence, a heterologous signal sequence may be added, such as the signal sequence for IL-7 described in U.S. Pat. No. 4,965,195; the signal sequence for IL-2 receptor described in Cosman et al., *Nature* 312:768 (1984); the IL4 signal peptide described in EP 367,566; the type I IL-1 receptor signal peptide described in U.S. Pat. No. 4,968,607; and the type II IL-1 receptor signal peptide described in EP 460,846.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express ITAK as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

As noted above, the present invention provides methods of detecting agonists or antagonists of ITAK, IL-1 and/or TNF-α. As used herein, "an ITAK agonist" does not include IL-1 or TNF-α. Such methods permit identification of elements of the signal transduction pathways of each of IL-1 and TNF-α.

In one embodiment, the invention thus generally provides a method for identifying gene products that associate with ITAK, comprising: (a) introducing nucleic acid sequences encoding an ITAK polypeptide into a first expression vector such that ITAK sequences are expressed as part of a fusion protein comprising a functionally incomplete first portion of a protein that is essential to the viability of a host cell; (b) introducing nucleic acid sequences encoding a plurality of candidate gene products that interact or associate with ITAK into a second expression vector such that any candidate gene products are expressed as part of a fusion protein comprising a second functionally incomplete portion of the protein that is essential to the viability of the host cell; (c) introducing the first and second expression vectors into a host cell under conditions and for a time sufficient such that host cell survival is dependent upon reconstitution of both the first and second functionally incomplete portions of the protein (that is essential to the viability of the host cell) into a functionally complete protein; and (d) identifying the nucleic acid sequences encoding the candidate gene products that associate with ITAK in the second expression vector.

For example, the yeast two-hybrid system (Fields and Song, Nature 340:245 (1989); U.S. Pat. No. 5,283,173 to Fields et al.) can be used to detect interactions between ITAK and other proteins or between ITAK and selected compounds, or pools of compounds, that are suspected of increasing or decreasing the activity of ITAK, IL-1 and/or TNF-α or of otherwise employing ITAK to transduce a biological signal. Such interactions can be detected by screening for functional reconstitution of a yeast transcription factor.

Briefly, the yeast two hybrid system was developed as a way to test whether two proteins associate or interact directly with each other and was then modified to serve as a method to "capture" candidate proteins that interact with a known protein of interest or "bait." The bait protein is expressed as a fusion protein with the DNA-binding domain of GAL4, a yeast transcription factor, in a specially designed yeast strain (Y190) containing reporter genes under GAL4 control. (Durfee et al, Genes & Devel. 7:555, 1993.) GAL4 is a modular yeast transcription factor with the DNA binding domain confined to the N-terminal 147 residues while the transcriptional activation function resides entirely in the C-terminal 114 residues. Libraries used in the two-hybrid system have clones expressing GAL4 activation domain fusion proteins. The method detects the reconstitution of GAL4 function when two fusion proteins encode proteins that associate with each other, so that the DNA-binding domain fusion recruits the activation domain fusion into position at the GAL4 promoter, leading to transcriptional activation of the GAL4-controlled reporter genes.

The ITAK nucleic acid sequences disclosed herein can be cloned into a suitable vector carrying the DNA-binding domain of GAL4 and transformed into an appropriate yeast strain to produce yeast cells which express a GAL4 DNA-binding domain/ ITAK region fusion protein using methods well known in the art. Activation domain cDNA libraries can then be screened in appropriate vectors. A positive signal in such a two-hybrid assay can result from cDNA clones that encode proteins that specifically associate with ITAK such as substrates or activators of ITAK. Knowledge of proteins that associate with ITAK can also permit searching for inhibitors of IL-1 and/or TNF-α signaling.

The functional interaction between ITAK and its associating proteins also permits screening for small molecules that interfere with the ITAK/substrate or ITAK/activator association and thereby inhibit IL-1 or TNF-α activity. For example, the yeast two-hybrid system can be used to screen for IL-1 and/or TNF-α inhibitors as follows. ITAK and activator/substrate, or portions thereof responsible for their interaction, can be fused to the GAL4 DNA binding domain and GAL4 transcriptional activation domain, respectively, and introduced into a strain that depends on GAL4 activity for growth on plates lacking histidine. Compounds that prevent growth can be screened in order to identify IL-1 and/or TNF-α inhibitors. Alternatively, the screen can be modified so that ITAK/activator or ITAK/substrate interaction inhibits growth, so that inhibition of the interaction allows growth to occur. Another, in vitro, approach to screening for IL-1 and/or TNF-α inhibition would be to immobilize one of the components, such as ITAK, or portions thereof, in wells of a microtiter plate, and to couple an easily detected indicator to the other component. An inhibitor of the interaction is identified by the absence of the detectable indicator from the well.

A high throughput screening assay can also be utilized to identify compounds that inhibit ITAK activity. For example, natural product extracts, from plant and marine sources, as well as microbial fermentation broths, can be sources of kinase inhibitors and can be screened for potential ITAK antagonists. Other sources of ITAK antagonists include preexisting or newly generated libraries of small organic molecules and preexisting or newly generated combinatorial chemistry libraries. Identification of endogenous ITAK substrate(s), and mapping of their phosphorylation site(s) to determine specific recognition motif(s), can enable the development of peptide mimetic inhibitors. In addition, in vivo regulation of ITAK activity likely involves endogenous protein inhibitor(s), which can be identified using the assay (s) described herein.

These assays also facilitate the identification of other molecules that interact with ITAK in a physiologically relevant manner, such as endogenous substrates, activators and the aforementioned natural protein inhibitors. Such molecules include, but are not limited to, receptors and receptor-associated polypeptides, guanine nucleotide binding proteins (G proteins), guanine nucleotide exchange factors (GEFs), guanine nucleotide activating proteins (GAPs), transcription activators, and repressors. Additionally, the ITAK assays can serve as readouts to identify other enzymes involved in a signaling cascade, such as other kinases, phosphatases and phospholipases.

Accordingly, the invention provides methods of detecting agonists or antagonists of ITAK, IL-1 and/or TNF-α by assaying the downstream response pathway effects of IL-1 or TNF-α signal transduction. In one aspect of the invention, the method for determining whether a selected agent is an ITAK agonist comprises (a) exposing the selected agent to an unstimulated ITAK response pathway under conditions and for a time sufficient to allow a stimulation of the pathway; and (b) detecting stimulation of the response pathway and therefrom determining the presence of an ITAK agonist. In a related aspect, the method for determining whether a selected agent is an ITAK agonist comprises (a) measuring the ITAK kinase activity of an ITAK response pathway; (b) exposing the selected agent to the measured ITAK response pathway; and (c) detecting increased ITAK kinase activity in the response pathway. Within another aspect, the invention also provides a method for determining whether a selected agent is an ITAK antagonist, comprising: (a) exposing the selected agent to an ITAK response pathway in the presence of an ITAK agonist under conditions and for a time sufficient to allow a decrease in stimulation of the pathway; and (b) detecting a decrease in the stimulation of the response pathway relative to the stimulation of the response pathway by the ITAK agonist alone, and therefrom determining the presence of an ITAK antagonist. Such methods may include assays of cellular proliferation (Raines et al., *Science* 243:393, 1989), prostaglandin production (Curtis et al., *Proc. Nat. Acad. Sci. USA* 86:3045, 1989), colony stimulating factor production (Curtis et al., 1989), cell surface immunoglobulin up-regulation (Giri et al., *J. Immunol.* 131:223, 1984), NFκ-B activation (Shirakawa et al., *Mol Cell. Biol.* 9:959, 1989), or other established biological signal transduction assays known to those skilled in the art.

In a related aspect, ITAK polypeptides according to the invention may be used for the structure-based design of an inhibitor of IL-1 or TNF-α downstream effects, as well as for the design of ITAK-inhibitors. Such structure-based design is also known as "rational drug design." Such design can include the steps of determining the three-dimensional structure of such an ITAK polypeptide, analyzing the three-dimensional structure for the likely binding sites of substrates (as well as analyzing ITAK for electrostatic potential of the molecules, protein folding, etc.), which sites represent predictive reactive sites, synthesizing a molecule that incorporates one (or more) predictive reactive site, and determining the ITAK-inhibiting activity of the molecule. (Sudarsanam et al., *J. Comput. Aided. Mol. Design* 6:223, 1992) ITAK polypeptides can be three-dimensionally analyzed by, for example, X-ray crystallography, nuclear magnetic resonance or homology modeling, all of which are well-known methods. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease.

Because only the cytokines IL-1 and TNF-α appear to induce ITAK activity, the present invention offers the advantage of selectively blocking functional cellular responses to these cytokines. Thus, ITAK facilitates the discovery of inhibitors of ITAK, and thus, inhibitors of the effects of excessive IL-1 and TNF-α release. This use of ITAK for the screening of potential inhibitors thereof is important and can eliminate or reduce the possibility of interfering reactions with contaminants.

Turning to another aspect of the invention, IL-1 activity is initiated by the IL-1 molecule binding to a membrane-bound IL-1 receptor, which in turn interacts with cytoplasmic proteins associated with the cytoplasmic region of the IL-1 receptor. For example, the cytoplasmic domain of the type I IL-1 receptor is associated with a GTP-ase activating protein (GAP) that is referred to herein as IIP1, and which is described in greater detail in an application entitled "IL-1 Receptor Interacting Protein" (U.S. Ser. No. 08/584,831, filed Jan. 11, 1996). GAP proteins, such as IIP1, interact with G proteins that in turn interact with cytoplasmic effector molecules (e.g., protein kinases or ion channels) that carry out early signaling functions. G-proteins bind to guanine nucleotides (GDP or GTP). When a G protein is bound to GTP it interacts with effector molecules to generate a biological signal (the "ON" configuration). Conversely, when a G-protein is bound to GDP, it does not interact and is not capable of generating a biological signal (the "OFF" configuration). G-proteins are in a constant state of equilibrium between the GTP-bound and GDP-bound forms. When IL-1 is not bound to IL-1 receptor, IIP1 catalyzes the hydrolysis of GTP to GDP, forcing the equilibrium between the GTP-bound and GDP-bound G-protein towards the GDP-bound "off" form, thereby preventing an IL-1 signal. When IL-1 binds to IL-1 receptor, the IIP1 interaction with GTP- and GDP-bound forms of the G-protein is interrupted, causing the equilibrium to shift towards the GTP-bound "on" form, and thereby transmitting an IL-1 signal. Thus, the net effect of IIP1 is to suppress the G-protein-linked signal.

A similar G-protein-regulated signaling pathway may control induction of ITAK activity in response to IL-1 or TNF-α. Conversely, the IL-1 or TNF-α-mediated induction of ITAK activity may control the function of one or more G-proteins. The disclosure herein of an ITAK polypeptide domain having pronounced amino acid sequence homology to known guanine nucleotide exchange factors (such as RCC1 (Bischoff and Ponstingl, *Nature* 354:80, 1991) is compatible with either of these schemes, which are not mutually exclusive. Thus, the provision herein of ITAK provides alternative avenues for the investigation, detection and possible control of G-protein-related pathways. ITAK may be used as a reagent to identify (a) a G protein that regulates—or is regulated by—ITAK and which is involved in IL-1 or TNF-α signaling, and (b) other proteins with which ITAK interacts that would be involved in IL-1 or TNF-α signal transduction pathways. These other proteins, including the G protein, are then useful tools to search for other inhibitors of IL-1 or TNF-α signaling. ITAK can also be used by coupling recombinant ITAK protein to an affinity matrix.

In another aspect, the present invention also provides nucleic acid probes based upon a nucleic acid molecule encoding ITAK. Such probes can be used in accordance with hybridization and other assays known in the art, for example, to detect ITAK genes in candidate samples, such as samples derived from candidate cell lines or animal strains or species. Such probes preferably specifically hybridize to the ITAK gene under appropriately determined conditions that may be conditions of moderate or high stringency (see, e.g., Sambrook et al., supra), and generally comprise at least about 15 nucleotides, typically at least about 18 nucleotides or at least about 20 nucleotides, and preferably from about 18 to about 35 nucleotides and even more preferably several hundred nucleotides. However, such probes can comprise up to an entire ITAK gene, if desired.

The present invention also provides antisense or sense nucleotides comprising a single-stranded nucleic acid sequence (either RNA or DNA) capable of binding to a target ITAK mRNA sequence (forming a duplex) or to the ITAK sequence in the double-stranded DNA helix (forming a triple helix). Such nucleotides often comprise a fragment of the coding region of ITAK cDNA but may also comprise a fragment of the non-coding region of ITAK cDNA. Typically such nucleotides comprise an ITAK-specific fragment. Such a fragment generally comprises at least about 15 nucleotides, typically at least about 18 nucleotides or at least about 20 nucleotides, and preferably from about 18 to about 35 nucleotides and even more preferably several hundred nucleotides. The ability to create an antisense or a sense nucleotide, based upon a cDNA sequence for a given protein, is described in, for example, Stein and Cohen, *Cancer Res.* 48:2659, 1988 and van der Krol et al., *BioTechniques* 6:958, 1988.

Binding of antisense or sense nucleotides to target nucleic acid sequences results in the formation of complexes that block translation (RNA) or transcription (DNA) by one of several means, including enhanced degradation of the duplexes, premature termination of transcription or translation, or by other means. The antisense nucleotides thus may be used to block expression of ITAK proteins.

Blockade of ITAK expression in this manner can be useful therapeutically in inflammatory disease situations. Antisense or sense nucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense nucleotides include those oligonucleotides that are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense nucleotides to modify binding specificities of the antisense or sense nucleotide for the target nucleotide sequence.

Antisense or sense nucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense nucleotides are preferably introduced into a cell containing the target nucleic acid sequence by insertion of the antisense or sense nucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense nucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense nucleotide or its conjugated version into the cell.

Alternatively, a sense or an antisense nucleotide may be introduced into a cell containing the target nucleic acid sequence by formation of a nucleotide-lipid complex, as described in WO 90/10448. The sense or antisense nucleotide-lipid complex is preferably dissociated within the cell by an endogenous lipase.

In another aspect, the present invention provides binding partners that specifically interact with ITAK. Such binding partners, typically antibodies, can be useful for inhibiting IL-1 or TNF-α activity in vivo and for detecting the presence of ITAK in a sample. Suitable ITAK-binding partners include antibodies that are immunoreactive with ITAK, and preferably monoclonal antibodies against ITAK, and other proteins that are capable of high-affinity binding to ITAK. The term "antibodies" includes polyclonal antibodies, monoclonal antibodies, fragments thereof such as F(ab')$_2$, and Fab fragments, as well as any recombinantly produced binding partners. Antibodies are defined to be specifically binding if they bind ITAK with a $K_a$ of greater than or equal to about $10^7$ $M^{-1}$. Affinities of binding partners or antibodies can be readily determined using conventional techniques, for example those described by Scatchard et al., *Ann. N.Y. Acad. Sci.* 51:660 (1949). Determination of other proteins as binding partners of ITAK can be performed using, for example, the yeast two-hybrid screening system described herein. The present invention also includes the use of ITAK, and peptides based on the amino acid sequence of ITAK, to prepare binding partners and antibodies that specifically bind to ITAK.

ITAK binding partners that are polyclonal antibodies can be readily generated from a variety of sources, for example, horses, cows, goats, sheep, dogs, chickens, rabbits, mice or rats, using procedures that are well-known in the art. In general, purified ITAK, or a peptide based on the amino acid sequence of ITAK that is appropriately conjugated, is administered to the host animal typically through parenteral injection. The immunogenicity of ITAK may be enhanced through the use of an adjuvant, for example, Freund's complete or incomplete adjuvant. Following booster immunizations, small samples of serum are collected and tested for reactivity to ITAK or the ITAK peptides. Examples of various assays useful for such determination include those described in: *Antibodies: A Laboratory Manual*, Harlow and Lane (eds.), Cold Spring Harbor Laboratory Press, 1988, as well as procedures such as counter-current immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530.

By virtue of the isolated ITAK provided herein, monoclonal antibodies specific for ITAK are readily prepared using well-known procedures, see for example, the procedures described in U.S. Pat. Nos. RE 32,011, 4,902,614, 4,543,439 and 4,411,993; Monoclonal Antibodies, Hybridomas: *A New Dimension in Biological Analyses*, Plenum Press, Kennett, McKearn, and Bechtol (eds.), 1980; Harlow, supra. Briefly, host animals such as mice are injected intraperitoneally at least once, and preferably at least twice at about 3 week intervals with isolated and purified ITAK or conjugated ITAK peptide, optionally in the presence of adjuvant. Mouse sera are then assayed by conventional dot blot technique or antibody capture (ABC) to determine which animal is best to fuse. Approximately two to three weeks later, the mice are given an intravenous boost of ITAK or conjugated ITAK peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as, $^{125}$I-ITAK is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas," *Strategies in Molecular Biology* 3:1–9 (1990). Similarly, binding partners can be constructed using recombinant DNA techniques to incorporate the variable regions of a gene that encodes a specific binding antibody. Such a technique is described in Larrick et al., *Biotechnology* 7:394 (1989).

Other types of "antibodies" may be produced using the information provided herein in conjunction with the state of knowledge in the art. For example, antibodies that have been engineered to contain elements of human antibodies that are capable of specifically binding ITAK are also encompassed by the invention.

Once isolated and purified, ITAK binding partners can be used to detect the presence of ITAK in a sample using established assay protocols. Further, the binding partners, typically the antibodies, of the invention may be used therapeutically to bind to ITAK and inhibit its activity in vivo. Such ITAK-binding partners can be bound to a solid phase such as a column chromatography matrix or a similar substrate suitable for identifying, separating or purifying molecular components obtained from cells that express ITAK. Adherence of ITAK or ITAK-binding proteins to a solid phase contacting surface can be accomplished by any means, for example, magnetic microspheres can be coated with ITAK-binding proteins and held in the incubation vessel through a magnetic field. Cell extracts are contacted with the solid phase that has ITAK or ITAK-binding proteins thereon. ITAK or ITAK-associated species bind to the fixed-binding protein and unbound material is then washed away. This affinity-binding method is useful for purifying, screening or separating such ITAK-associated molecules from solution. Methods of releasing positively selected components from the solid phase are known in the art and encompass, for example, the use of pH changes, altered salt concentration, or chaotropic agents.

ITAK or a fragment or variant thereof can also be useful itself as a therapeutic agent in inhibiting IL-1 and/or TNF-α signaling. ITAK agonists or ITAK antagonists provided by the invention are also useful as therapeutic agents in inhibiting IL-1 and/or TNF-α signaling, alone or in combination with ITAK or a fragment thereof or a variant thereof. ITAK, or an ITAK agonist or an ITAK antagonist, is introduced into the intracellular environment by well-known means, such as by encasing ITAK (or its agonist or antagonist) in liposomes or coupling it to a monoclonal antibody targeted to a specific cell type.

When used as a therapeutic agent, ITAK, an ITAK agonist, or an ITAK antagonist can be formulated into pharmaceutical compositions according to known methods. In a preferred embodiment, the ITAK contains a mutation of the lysine residue at position 81 to another amino acid, for example the ITAK variant known as ITAK A81, which contains a mutation from lysine to alanine. ITAK, an ITAK agonist, or an ITAK antagonist can be introduced into the intracellular environment using methods well known in the field, such as encasing ITAK in liposomes or coupling ITAK to a monoclonal antibody targeted to a specific cell type.

ITAK, an ITAK agonist, or an ITAK antagonist can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain ITAK, or an ITAK agonist or an ITAK antagonist, complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of ITAK.

Compositions of the invention that are nucleotide sequences encoding ITAK or a fragment thereof, an ITAK variant or a fragment thereof, an ITAK agonist or a fragment thereof, or an ITAK antagonist or a fragment thereof, are used as therapeutic agents according to gene therapy strategies. Generally such nucleotide sequences are incorporated into vectors leading to expression of the desired nucleotide sequences; such vectors are readily constructed by those skilled in the art. In addition, administration of such vectors by various means is well known to those skilled in the art.

Such vectors for gene therapy may be retroviral vector constructs or may be developed and utilized with other viral carriers including, for example, poliovirus (Evans et al., Nature 339:385–388, 1989; and Sabin, J. Biol. Standardization 1:115–118, 1973); rhinovirus; pox viruses, such as canary pox virus or vaccinia virus (Fisher-Hoch et al., PNAS 86:317–321, 1989; Flexner et al., Ann. N.Y. Acad. Sci. 569:86–103, 1989; Flexner et al., Vaccine 8:17–21, 1990; U.S. Pat. Nos. 4,603,112 and 4,769,330; WO 89/01973); SV40 (Mulligan et al., Nature 277:108–114, 1979); influenza virus (Luytjes et al., Cell 59:1107–1113, 1989; McMichael et al., N. Eng. J. Med. 309:13–17, 1983; and Yap et al., Nature 273:238–239, 1978); adenovirus (Berkner, Biotechniques 6:616–627, 1988; Rosenfeld et al, Science 252:431–434, 1991); parvovirus such as adeno-associated virus (Samulski et al., J. Vir. 63:3822–3828, 1989; Mendelson et al, Virol. 166:154–165, 1988); and herpes (Kit, Adv. Exp. Med. Biol. 215:219–236, 1989).

Once a vector has been prepared, it may be therapeutically administered to a warm-blooded animal. As noted above, methods for administering a vector are well known to those skilled in the art and include, for example, by direct administration, or via transfection utilizing various physical methods, such as lipofection (Felgner et al., Proc. Natl. Acad. Sci. USA 84:7413–7417, 1989), direct DNA injection (Acsadi et al., Nature 352:815–818, 1991); microprojectile bombardment (Williams et al, PNAS 88:2726–2730, 1991); liposomes (Wang et al., PNAS 84:7851–7855, 1987); $CaPO_4$ (Dubensky et al., PNAS 81:7529–7533, 1984); or DNA ligand (Wu et al., J. Biol. Chem. 264:16985–16987, 1989).

Pharmaceutical compositions for gene therapy comprising one of the above-described recombinant viruses containing nucleotide sequences encoding ITAK or a fragment thereof, an ITAK variant or fragment thereof, an ITAK agonist or a fragment thereof, or an ITAK antagonist or fragment thereof are provided. The composition may be prepared either as a liquid solution, or as a solid form (e.g., lyophilized) which is suspended in a solution prior to administration. In addition, the composition may be prepared with suitable carriers or diluents for either injection, oral, or rectal administration. Generally, the recombinant virus is utilized at a concentration ranging from 0.25% to 25%, and preferably about 5% to 20% before formulation. Subsequently, after preparation of the composition, the recombinant virus will constitute about 1 μg of material per dose, with about 10 times this amount material (10 μg) as copurified contaminants. Preferably, the composition is prepared in 0.1–1.0 ml of aqueous solution formulated as described below.

Pharmaceutically acceptable carriers or diluents are non-toxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2 and 150 mM NaCl. In this case, since the recombinant vector represents approximately 1 μg of material, it may be less than 1% of high molecular weight material, and less than 1/100,000 of the total material (including water). This composition is stable at −70° C. for at least six months. The composition may be injected intravenously (i.v.), subcutaneously (s.c.), or intramuscularly (i.m.). Oral formulations may also be employed with carriers of diluents such as cellulose, lactose, mannitol, poly (DL-lactide-co-glycolate) spheres, and/or carbohydrates such as starch. The composition may take the form of, for example, a tablet, gel capsule, pill, solution, or suspension, and additionally may be formulated for sustained release. For rectal administration, preparation of a suppository may be accomplished with traditional carriers such as polyalkalene glucose, or a triglyceride.

The following Examples provide an illustration of embodiments of the invention and should not be construed to limit the scope of the invention which is set forth in the appended claims. In the following Examples, all methods described are conventional unless otherwise specified.

EXAMPLES

Example 1

Determination of ITAK Activity

Cloned ITAK gene sequences were initially detected by comparative analysis of the partial amino acid sequence of an isolated and purified rabbit IL-1-induced β-casein kinase polypeptide, IL-1/TNF-α-activated kinase (ITAK). Cloned human nucleotide sequences were identified that encoded polypeptide regions characteristic of protein kinases and that displayed amino acid sequence homology with ITAK-derived peptides.

ITAK activity was originally detected by its ability to phosphorylate intact β-casein (Guesdon et al., *J. Biol. Chem.* 268:4236 (1993); Guesdon et al., *Biochem. J.* 304:761 (1994)). However the assay utilized throughout this purification is a second generation peptide-based assay. Three sites (Ser 57, Ser 124, and Ser 142) of ITAK-mediated phosphorylation of β-casein were identified using methods known in the art. Dephosphorylated bovine β-casein was then $^{32}$P-labeled with ITAK under previously described conditions (Guesdon et al., 1993; Guesdon et al., 1994; supra). Radiolabeled β-casein was proteinase digested and the resultant peptides were separated by two-dimensional thin layer chromatography and/or reverse phase high performance liquid chromatography (RP-HPLC). Isolated, radioactive peptides were then sequenced to determine the amino acid sequences of phosphorylation acceptor sites. Three peptides containing phosphoserine were identified in this manner. Various peptide substrates composed of sequences around and including these three serine residues were synthesized on an ABI Model 430 Peptide Synthesizer. All peptide substrates were synthesized having multiple N-terminal or C-terminal basic residues to mediate peptide binding to phosphocellulose filters; this is a commonly used approach in peptide-based kinase assays. (Glass et al., *Anal. Biochem.* 87:566,1978; Casnellie et al., *Proc. Nat. Acad. Sci. USA* 79:282, 1982.) Kinetic analysis of the various potential peptide substrates resulted in selection of the following peptide for the standard ITAK assay:

Arg-Arg-Arg-His-Leu-Pro-Pro-Leu-Leu-Leu-Gln-Ser-Trp-Met-His-Gln-Pro-His-Gln (single letter code: RRRHLPPLLLQSWMHQPHQ) (SEQ ID:NO 3)

In the standard ITAK assay, 10 μl of ITAK-containing sample is added to 10 μl of 2× assay buffer (40 mM Hepes, pH 7.4/20 mM MnCl$_2$/20 μM ATP/1 μCi γ-($^{32}$P)-ATP) containing 2 mM peptide substrate, the reaction proceeds for 20 minutes at 30° C., then is stopped by adding 10 μl of formic acid. Blank controls consist of assays performed in the absence of peptide substrate. After reactions are stopped, assay mixtures are spotted onto circular 2.5 cm phosphocellulose filters (P81, Whatman, Fairfield, N.J.), washed twice with 75 mM H$_3$PO$_4$, and placed in 20 ml borosilicate scintillation vials for Cerenkov counting in a β-counter. Net counts per minute, cpm, (sample cpm minus blank cpm) are used to calculate picomoles of phosphate incorporated into the peptide substrate. One Unit of ITAK activity is defined as that amount of ITAK necessary to incorporate 1 picomole of phosphate into the peptide substrate, RRRHLP-PLLLQSWMHQPHQ (SEQ ID:NO 3), in one minute under standard assay conditions. Specific activity is defined as Units of ITAK activity per milligram of protein. Adaptations of this assay for large scale screening may include use of biotinylated ITAK substrate peptide in a scintillation proximity assay (SPA) with streptavidin coated SPA beads, or covalent modification of the ITAK substrate peptide with fluorescent tags by techniques known in the art.

Example 2

Purification of ITAK

This example describes the purification of IL-1-induced, rabbit lung ITAK in quantities sufficient to permit partial amino acid sequencing of the ITAK protein (see Table 1). Rabbit lungs were chosen because they displayed the greatest increase in ITAK activity in response to IL-1α, when compared with untreated control animal tissues. This example details the purification of ITAK from 70 pairs of lungs taken from IL-1α-treated rabbits.

Briefly, New Zealand White rabbits (2.0–2.5 kg) were intravenously ear injected with 100 μg of human recombinant IL-1α/kg body weight in a total volume of 0.5 ml in PBS (phosphate buffered saline). Fifteen minutes after injection animals were sacrificed by cervical dislocation and the lungs rapidly excised (within 2–3 min). Once removed, lungs were fast-frozen on dry ice, then stored at −80° C.

Lungs were cut into small pieces (~0.5 cm$^3$) while the tissue was still partially frozen, in ice-cold Wash Buffer (PBS containing proteinase inhibitors, 0.1 mM leupeptin and 1.0 mM phenylmethylsulfonyl fluoride (PMSF)) on ice. Minced lungs were washed at least twice, to remove contaminating blood proteins, with 100 ml of ice cold Wash Buffer/pair of lungs. Generally five pairs of lungs were processed at a time; therefore each wash was performed in 500 ml of Wash Buffer, for ten minutes with constant agitation, after which buffer was removed by decanting and aspiration.

Following the second wash, minced lung tissue was immediately placed in ice-cold Homogenization Buffer (HB: 25 mM Tris-HCl, pH 7.5/100 mM β-glycerophosphate/25 mM para-nitrophenyl phosphate/10 mM sodium orthovanadate/2 mM DTT (dithiothreitol)/1 mM MgCl$_2$/5 mM EDTA (Ethylenediaminetetraacetic Acid)/5 mM EGTA (Ethylene Glycol-bis(β-aminoethyl) Ether) N,N,N',N'-Tetraacetic Acid)/5 mM benzamidine/1 μM E-64 (trans-Epoxysuccinyl-L-leucylamido-(4-guanidino)butane)/1 mM PMSF/0.1 mM leupeptin), and further minced. Minced lungs were homogenized at a final ratio of 10:1 (vol. HB (ml): mass tissue (gm)). Initially, the minced lungs were homogenized in 75% of the total volume of HB, solid material was pelleted by centrifugation at 12,000 rpm for 30 min at 4° C. and the pellets re-homogenized in the remaining 25% of the buffer.

Homogenization (of the minced tissue in 75% of the buffer) was performed using a Brinkman Homogenizer at setting #8 for two 20 second pulses. Solid material was removed by centrifugation at 12,000 rpm for 30 minutes at 4° C. The supernatant was removed, pellets resuspended in the remaining 25% of the HB and re-homogenized at setting #8 for 30 seconds. Another centrifugation at 12,000 rpm for 30 minutes at 4° C. was used to remove insoluble material. Both supernatants were combined and further clarified by gravity filtration through glass wool.

This preparation, which utilized 70 pairs of lungs (wet weight 560 grams) isolated from rHuIL-1α-treated rabbits, yielded 5.7 liters of lung homogenate. The lung homogenate was made 25% with respect to ammonium sulfate by the gradual addition of 764 gm of solid ammonium sulfate with constant, slow stirring at 4° C. Once all of the ammonium sulfate was in solution, stirring was stopped and the homogenate incubated at 4° C. overnight. The 0–25% ammonium sulfate precipitate was collected by centrifugation at 12,000 rpm for 30 min at 4° C. Pelleted precipitates were resolubilized, in four equal batches, in 500 ml each of Buffer A (20 mM Tris, pH 8.5/50 mM β-glycerophosphate/2 mM DTT/1 mM EDTA/1 mM EGTA/0.1 mM PMSF/0.1 mM leupeptin). The resolubilized 0–25% precipitate was dialyzed against two changes (10 liters each) of Buffer A at 4° C. overnight. After dialysis, residual insoluble material was removed by centrifugation at 20,000 rpm for 30 min at 4° C. The resultant supernatant was sequentially filtered through a glass fiber pre-filter, a 0.8 µm filter, and finally a 0.45 µm filter (Corning, Corning, N.Y.).

Buffers used for all chromatography were filtered through 0.45 µm filters (Corning) prior to use. Each of the four filtered batches (containing 550–600 ml) was individually applied to a 25 ml (10.5×1.6 cm) column of Source 15Q (Pharmacia, Piscataway, N.J.) previously equilibrated with Buffer A, at a flow rate of 6.0 ml/min. The column was then washed with ten bed volumes (250 ml) of Buffer A at 6.0 ml/min. Bound protein was eluted with an increasing linear gradient of NaCl (0–0.5 M) in Buffer A at 6.0 ml/min over a period of 56.6 minutes. Four and a half ml fractions were collected and ten µl from each fraction assayed for ITAK activity. All chromatographic steps were performed at 4° C., unless otherwise indicated.

ITAK activity eluted from Source 15Q at a NaCl concentration of 200–300 mM (Table 1). Fractions containing eluted ITAK activity from the four separate Source 15Q runs were pooled, diluted 1:2 with Buffer B (Buffer A containing 10% glycerol) and applied to a 50 ml (9.5×2.6 cm) column of Reactive Green 19 (Sigma, St. Louis, Mo.), previously equilibrated with Buffer B, at a flow rate of 2.5 ml/min. After loading, the column was washed with four bed volumes (200 ml) of Buffer B at 2.5 ml/min. Protein was eluted from the Green 19 column with an increasing linear gradient of NaCl (0–2.0 M) in Buffer B at 2.5 ml/min over 80 min. Four-ml fractions were collected and 5 µl aliquots from each fraction assayed for ITAK activity. ITAK activity eluted in a broad peak with a NaCl concentration of from 1.0–1.5 M. Active fractions were pooled and concentrated in a Centriprep 30 concentrator (Amicon, Beverly, Mass.) to a final volume of 5.0 ml.

The ITAK concentrate was loaded onto a HiLoad 26/60 Superdex 200 size exclusion chromatography column (Pharmacia, Piscataway, N.J.) previously equilibrated with Buffer B. Protein was eluted with Buffer B at 2.5 ml/min. Fractions of 4.0 ml were collected and 5 µl aliquots assayed for ITAK activity. Gel filtration calibration standards (BioRad, Hercules, Calif.) chromatographed under identical conditions were used to estimate the apparent molecular weight of ITAK; its elution was consistent with a Mr~350 kD.

The pooled peak fractions of ITAK activity eluted from Superdex 200 were made 0.1% in NP-40 by addition of the appropriate amount of a 10% NP-40 solution (Pierce, Rockford, Ill.), incubated at 37° C. for 5 minutes, then immediately applied onto a 25 ml (12.5×1.6 cm) column of Heparin-Sepharose (Pharmacia) previously equilibrated with Buffer C (Buffer B containing 0.1% NP-40), at a flow rate of 2.0 m/min. This step and all subsequent chromatographic steps were conducted at room temperature (20° C.). After loading, the column was washed with four column volumes (100 ml) of Buffer C at the same flow rate. The column was developed with an increasing linear gradient of NaCl (0–1.0 M) in Buffer C at 2.0 ml/min over 50 min. One ml fractions were collected throughout the salt gradient and 2 µl from each fraction assayed for ITAK activity. ITAK eluted in the 175–250 mM NaCl region of the gradient.

Active fractions were combined and diluted 1:5 with Buffer C pH adjusted to 8.0, incubated at 37° C. for 5 minutes, then immediately applied to a 1.0 ml HR5/5 MonoQ column (Pharmacia), previously equilibrated with Buffer C pH 8.0, at 1.0 ml/min. The column was washed at 1.0 m/min with 10 column volumes (10 ml) of Buffer C pH 8.0, before being developed with an increasing linear gradient of NaCl (0–0.5 M) in Buffer C pH 8.0, also at 1.0 ml/min for 20 minutes. Fractions of 0.5 ml were collected throughout the salt gradient and 1 µl from each assayed for ITAK activity (Table 1). ITAK activity eluted as a single, well-resolved peak in the 200–250 mM NaCl portion of the gradient An additional 1 µl was removed from each fraction for analysis by sodium dodecyl sulfate polyacrylamide gel electrophoresis (SDS-PAGE), using pre-cast 8–16% Novex (San Diego, Calif.) gradient gels.

Prior to SDS-PAGE the 1 µl ITAK-containing fractions from the MonoQ column were incubated under modified kinase assay conditions (20 mM Hepes-pH 7.4/10 mM MnCl$_2$/10 µM ATP/0.5 µCi γ-($^{32}$P)-ATP, for 45 min at 30° C.) in the absence of exogeneously added substrate. This procedure had previously resulted in the $^{32}$P-labeling of endogeneous moieties estimated to be ~110–125 kD. Following electrophoresis the gel was silver stained and the radiolabeled band(s) identified using a PhosphorImager (Molecular Dynamics, Sunnyvale, Calif.). Prominent silver stained bands estimated to be 90, 100 and 110 kD were observed to correspond with ITAK activity. The 110 kD band and two poorly stained bands at 120 and 125 kD migrated to positions on the gel coinciding with the $^{32}$P-labeled moieties. All molecular weight estimates were based on direct comparison with Novex Wide Range Protein Standards electrophoresed on the same gel.

Eluted MonoQ column fractions having ITAK activity were combined, pH adjusted to 7.0 with 2.0 M Tris-HCl, pH 7.0, then applied in four separate batches (300–400 µl each) to a 60×0.75 cm Bio-Sil SEC-400 HPLC gel filtration column (BioRad, Hercules, Calif.) previously equilibrated with Buffer D (20 mM Tris-HCl, pH 7.0/10 mM β-glycerophosphate/1 mM DTT/1 mM EDTA/1 mM EGTA/1 mM PMSF/0.1 mM leupeptin/10% glycerol/0.1% NP-40). Proteins were eluted from the column at a flow rate of 0.5 m/min, 0.5 ml fractions were collected, and 0.5 µl from each fraction assayed for ITAK activity. An additional 0.5 µl was used for $^{32}$P radiolabeling with γ-($^{32}$P)-ATP under modified kinase assay conditions without exogenous substrate, SDS-PAGE and silver staining as described above. Again the 90 and 100 kD bands co-eluted with ITAK activity, as did the endogenously $^{32}$P-labeled 110, 120 and 125 kD bands. Gel filtration calibration standards (BioRad) were chromatographed under identical conditions immediately after the final ITAK run. ITAK (Table 1) eluted from the Bio-Sil SEC-400 column (all four runs) at an elution volume consistent with a M,=350 kD.

ITAK-containing fractions from the HPLC gel filtration column were combined and applied to a 35 µl (5×0.1 cm) microbore MonoQ (Pharmacia) column previously equilibrated with Buffer E (20 mM Tris-HCl, pH 8.5/10 mM β-glycerophosphate/1 mM DTT/1 mM EDTA/1 mM EGTA/1 mM PMSF/ 0.1 mM leupeptin/10% glycerol/0.1% NP-40). ITAK was applied to the column at 50 µ/min; multiple loadings were necessary and in each case the column was washed with Buffer E until the absorbance at 280 nm returned to baseline. After the final loading the column was washed with an additional 30 column volumes of Buffer E. All loadings and washings were performed at a flow rate of 50 µl/min. Protein was eluted from the column with a steep increasing linear gradient of NaCl (0–0.5 M) in Buffer E at a flow rate of 50 µl/min over a period of 10 min. Fractions of 50 µl were collected and 0.25 µl was removed from each fraction to assay for ITAK activity. An additional 0.25 µl was removed for $^{32}$P radiolabeling with γ-($^{32}$P)-ATP under modified kinase assay conditions without exogenous substrate, SDS-PAGE and silver staining as detailed above.

Virtually all (>95%) of the ITAK activity eluted in a single fraction (Fraction #12, Table 1) which contained the previously observed unlabeled 90 and 100 kD bands as well as the ($^{32}$P)-labeled 110, 120 and 125 kD bands. Approximately one third of the ITAK containing fraction was used for preparative gel electrophoresis. The sample was first endogenously labeled with $^{32}$P as described above, after which it was reduced (with excess DTT at 100° C. for 30 min) and then alkylated with an excess of iodoacetamide for 15 minutes in the dark. Electrophoresis was performed using 8–16% pre-cast Novex gradient gels and run at 100 V (constant voltage) for 30 min, then at 150 V (constant voltage) for an additional 90 min. Following electrophoresis the gel was stained with Coomassie Brilliant Blue G-250, destained, Saran-wrapped and exposed to a Storage Phosphor Screen for PhosphorImager identification of the radiolabeled band(s). Those bands co-purifying with ITAK activity, including the radiolabeled bands, were excised from the gel for in-gel trypsin digestion using a modification of techniques known in the art. (Henzel et al., in Methods: A Companion to Methods in Enzymology 6, pp. 239–247, 1994.)

Three slices excised from radioactive regions of the gel were estimated to contain proteins having molecular masses of 110, 120 and 125 kD, based on comparison with co-electrophoresed Wide Range Protein Standards (Novex, San Diego, Calif.). These gel slices were Cerenkov counted and contained 3.0×10$^5$, 6.9×10$^5$ and 8.3×10$^5$ cpm, respectively. In-gel trypsin digestion was performed on these gel slices using sequencing grade trypsin (Promega, Madison, Wisc.) at a 1:10 (w/w) ratio. Digestion was performed in 20 mM NH$_4$HCO$_3$, pH 8.0 at 37° C. for 16 hours. The resultant peptides were isolated from the gel bits by extraction with 60% acetonitrile/5% formic acid using both incubation at 37° C. and sonication to facilitate recovery of peptides.

Recovered peptides were briefly vacuum concentrated (Speed-Vac SC 100, Savant, Farmingdale, N.Y.) to remove the majority of acetonitrile, then separated by applying the material to a capillary C$_{15}$ (Vydac, Hesperia, Calif.) column previously equilibrated with 0.1% trifluoroacetic acid (TFA) at a flow rate of 15 µl/min. After loading, the capillary column was exhaustively washed with 0.1% TFA at 15 µl/min. Peptides were eluted with an ascending gradient of acetonitrile (0–90%, 1.0% per minute) over 90 min. Eluted peptides were monitored spectrophotometrically at 214 nm and fractions hand collected. Tryptic peptide maps of the 110 and 120 kD bands were virtually identical and the map of the 125 kD band was similar though less well defined, suggesting that these three bands were likely modified forms of the same protein. A small portion of each fraction (3–5%) was analyzed by MALDI (matrix-assisted laser desorption mass spectroscopy) using a Lasermat Mass Analyzer (Finnigan MAT) and/or by triple quadrapole mass spectroscopy (Finnigan MAT TSQ 700 with electrospray ionization), and the remainder was sequenced by Edman degradation using either an ABI 476A or an ABI 494 automated protein sequencer. These further analyses of peptides derived from the three radiolabeled bands corroborated the hypothesis that the 110, 120 and 125 kD bands are related.

ITAK was found to contain the following sequences:

(SEQ ID:NO 4)
Gly-Ala-Phe-Gly-Glu-Ala-Thr-Leu-Tyr-Arg (SEQ ID:NO 5)
Val-Thr-Leu-Leu-Asn-Ala-Pro-Thr-Lys

Based on homology to other kinases, the sequence depicted as SEQ ID:NO 4 resembles a truncated version of a kinase signature motif. (Hanks et al., Science 241:42, 1988.) The presence of this rabbit ITAK sequence fragment, which identified this molecule as a kinase, permitted comparison to the sequences of cDNA clones, derived from independent biological source materials, that also contained kinase motifs (See Examples 3, 4). The translation of one such partial clone, generated from a subtracted human dendritic cell cDNA library and called HH0381, revealed that this cDNA clone contained sequences identical to SEQ ID:NO 4. An extended version of the HH0381 cDNA called clone 7 was found to contain human cDNA-derived nucleotide sequences that translated to both of the amino acid sequences shown in SEQ ID:NOS 4 and 5, which were identified in purified rabbit ITAK peptides. In addition, other amino acid sequences present among the tryptic peptides generated from purified rabbit lung 110, 120 and 125 kD ITAK were also found encoded by clone 7. These shared sequences are depicted here as SEQ ID:NO 6 and SEQ ID:NO 7.

Ser-Ser-Thr-Val-Thr-Glu-Ala-Pro-Ile-Ala-Val-Val-Thr-Ser-Arg  (SEQ ID:NO 6)

Leu-Gly-Leu-Asp-Ser-Glu-Glu-Asp-Tyr-Tyr-Thr-Pro-Gln-Lys-Val-Asp-Val-Pro-Lys  (SEQ ID:NO 7)

TABLE 1

Isolation and Purification of ITAK From IL-1α-Induced Rabbit Lung

| Preparation | total protein (mg) | volume (ml) | protein conc. (mg/ml) | activity (Units) | Spec. Act. (Units/mg) | fold purif. |
|---|---|---|---|---|---|---|
| total lung homogenate | 57300 | 5700 | 10.05 | [0] | 0.43 | 1 |
| S15Q load (0–25% ammSO4 pellet) | 1510 | 2040 | 0.74 | [0] | 16.5 | 38 |
| Green 19 load | 333 | 241 | 1.38 | 19039 | 57.1 | 133 |
| Superdex 200 load | 112 | 52 | 2.15 | {5474} | 222.1 | 517 |
| Heparin Sepharose load | 9.4 | 20 | 0.47 | 24851 | 2646 | 6153 |
| Mono Q, pH 8.0 load | *1 | 70 | 0.014 | 5345 | 5345 | 12430 |
| SEC-400 load | 0.225 | 1.35 | 0.167 | 4105 | 18244 | 42428 |
| microMono Q load | 0.14 | 10.6 | 0.013 | 6477 | 46254 | 107591 |
| microMono Q fraction #12 | $0.1 | 0.062 | 1.61 | 9844 | 98640 | 229395 |

*estimated, too dilute to get accurate measurement
$estimate based on A @280 nm and silver staining
[ ] unable to assay due to high background and inhibition
{ } aberrantly low, SA based on HS load

Example 3

Identification of Human Kinase Gene Sequence in A Human Dendritic Cell cDNA Library Human dendritic cells (DC) were purified from freshly collected human bone marrow as follows.

Bone marrow cells were fractionated on a Ficoll density gradient, and CD34+ bone marrow cells were isolated from the high density (buffy coat) fraction using a Ceprate LC CD34 biotin kit (CellPro, Bothell, Wash.) according to the manufacturer's instructions. Briefly, buffy coat cells were incubated with biotinylated monoclonal anti-CD34 antibody, washed in buffer containing normal saline, and the cell suspension applied to a column of solid-phase immobilized streptavidin. CD34+ cells were adsorbed to the column by streptavidin-biotin affinity binding while CD34− cells washed through in the column effluent. Positively slected CD34+ cells were then mechanically desorbed from the flexible column by squeezing it, because the streptavidin-biotin interaction is of higher affinity than that between the antibody and its cognate ligand, CD34.

CD34+ cells were cultured at 37° C. in a humidified incubator (10% $CO_2$) for two weeks in Super McCoy's medium supplemented with 10% fetal calf serum, 20 ng/ml granulocyte-macrophage colony stimulating factor, 20 ng/ml IL-4, 20 ng/ml TNF-α, and 100 ng/ml FLT3 ligand. Viable cells recovered from cultures were further selected for expression of the known DC cell surface markers CD1a and HLA-DR by fluorescence-activated cell sorting (FACS) using antibodies specific for these markers.

Total CD1a+/HLA-DR+ DC RNA was isolated by guanidinium thiocyanate-cesium chloride gradient centrifugation (standard protocol, see Sambrook et al., Molecular Cloning: A Laboratory Manual, $2^{nd}$ Ed., Cold Spring Harbor Laboratory Press (1989)). Polyadenylated RNA was purified on oligo dT-coupled latex beads (Qiagen, Chatsworth, Calif.), according to manufacturer's instructions. A DC cDNA library in plasmid pBluescriptSK(−) (Stratagene, La Jolla, Calif.) was prepared essentially as described in Larsen et al., J. Exp. Med. 172:159 (1990). Briefly, approximately 1 μg of polyA+ DC RNA was converted to double stranded cDNA using random hexamer primers and reverse transcriptase using a Timesaver cDNA kit (Pharmacia, Piscataway, N.J.).

The cDNA reactions were optimized to generate an average cDNA size of about 400 bp. The double-stranded cDNA was modified with BglII adapters (described in Larsen et al., supra) and ligated to pBluescriptSK(−) that had been linearized with BamHI and similarly modified with BglII adapters. The recombinant constructs were transformed into E. coli.

Subtractive hybridization of the human DC cDNA library was conducted using a human fibroblast cDNA library to enrich for cDNAs preferentially contained in the DC library. In brief, the DC cDNA library in pBluescript was converted to single-stranded phagemid, and the single-stranded phagemid was subtracted with biotinylated RNA transcribed from the inserts of a driver cDNA library prepared from human foreskin fibroblasts in a modified λgt10 vector containing an SP6 RNA polymerase promoter. For a general description of the methods involved, see Klar et al. (Cell 69:95 (1992)) and Owens et al. (Mol. Cell. Biol. 11:4177 (1991)). Single-stranded phagemids recovered from subtraction were retransformed into E. coli. Individual colonies were isolated, and plasmid DNA was prepared and sequenced using dye terminator methodology (ABI Prism DyeDeoxy Kit, Perkin-Elmer, Foster City, Calif.).

Each plasmid was sequenced in one direction using a vector-specific primer adjacent to the BamHI cloning site. Sequences were compared to non-redundant protein and nucleotide database sequences (National Ctr. for Biotechnol. Information (NCBI), Bethesda, Md.) using the BLAST algorithm. (Altschul et al., J. Mol. Biol. 215:403, 1990. ) Translation of the ITAK cDNA insert of clone HH0381 (542 nt) revealed that it encoded the GAFGEATLYR amino acid sequence (SEQ ID:NO 4) previously detected in a rabbit lung ITAK tryptic peptide. (See Example 2.) The translated HH0381 sequence also showed homology to catalytic domains of several protein kinases in the NCBI database. The HH0381-encoded partial ITAK amino acid sequence showed the strongest sequence homology (greater than 30% identity) with a corresponding region of the murine nek1 protein (Letwin et al., EMBO J. 11:354, 1992), among protein kinase sequences in the database.

Example 4

Cloning of Full Length Gene Encoding ITAK

To identify the full length human gene encoding ITAK, the HH0381 human cDNA cloned insert was $^{32}$P labeled by random priming according to standard procedures (Sambrook et al., supra) for use as a probe to screen a human dendritic cell cDNA library prepared using the λZAPII vector (Stratagene, La Jolla, Calif.) according to the manufacturer's recommendations. Briefly, the cDNA insert of clone HH0381 (542 bp) was excised from the plasmid, gel-purified, radiolabeled with $^{32}$P using a Prime-It II kit (Stratagene, La Jolla, Calif.), and used to probe another DC cDNA library prepared in bacteriophage lambda vector λZAPII (Stratagene). This second DC cDNA library was prepared from the same DC mRNA as the DC library described above, except a cDNA fraction having a larger average size (about 1000 bp, instead of 400 bp) was used. The cDNA ends were modified with EcoRI adapters included in the Timesaver cDNA synthesis kit (Pharmacia), and the ligated to EcoRI-digested λZAPII. One positive clone was selected on the basis of hybridization to the HH0381-derived probe and isolated by successive rounds of purification and re-hybridization. The insert of this clone, designated clone 7, was sequenced using dye terminator methodology.

FIG. 1 (SEQ ID:NO 8) shows a composite nucleotide sequence of the ITAK-coding strands of the cDNA insert of clone 7 (nucleotides 1–2040), and clone 16-1 (nucleotides 2041–3264). The translated amino acid sequence (640 amino acids) of the open reading frame is depicted below the corresponding nucleotide sequence. Examination of the clone 7 insert DNA coding sequence showed that upon translation into an amino acid sequence, it encoded the kinase signature peptide sequence GRGAFGEATLYR (Hanks et al., Science 241:42, 1988), a portion of which, GAFGEATLYR, had been identified in a rabbit ITAK tryptic peptide as SEQ ID:NO 4. (See Example 2.) The amino acid sequences of additional rabbit ITAK tryptic peptides were also found to be encoded by portions of the human clone 7 DNA sequence, including the ITAK peptides of SEQ ID:NOS 4–7. While clone 7 included sequences encoding an initiator methionine residue, it did not appear that clone 7 contained DNA sequences encoding the full ITAK open reading frame (ORF).

In order to identify the sequences encoding the remainder of the ITAK ORF, a new DNA probe was designed from the clone 7 sequence data for use in hybridization to additional human cDNA libraries. A 918 bp DNA probe was prepared from the clone 7 insert sequence as follows: First, the fragment was amplified by polymerase chain reaction (PCR) using the indicated primers:

a) 5' primer: CCATGGCTGAGACGCTTG          (SEQ ID:NO 9)

b) 3' primer: GTCGTCCATATTCGCCACAG        (SEQ ID:NO 10)

Template DNA (~2×10$^6$ phage) consisted of a human cDNA library made in λgt10 from the human epidermal carcinoma cell line KB (ATCC CCL17). A 50 μl amplification reaction contained template (~2×10$^6$ phage) plus 25 pmol of each primer, 10 mM Tris-HCl, pH 8.3, 1.5mM MgCl$_2$, 50 mM KCl, 200 μM each dATP, dGTP, dCTP, dTTP, and 2.5 units of Taq polymerase (Boehringer Mannheim, Indianapolis, Ind.). Reactions conditions were: 1 cycle of (5 min, 94° C.; 1 min, 64° C.; 2 min, 72° C.); 29 cycles of (1 min, 94° C.; 1 min, 64° C.; 2 min, 72° C.); followed by 5 min, at 72° C.

Second, a probe was made from this amplified, clone 7-derived fragment by using 7.5 ng of the fragment as template in a 100 μl amplification reaction containing 50 pmol of the 3' primer (GTCGTCCATATTCGCCACAG) (primer (b) above; (SEQ ID:NO 10)), 10 mM Tris-HCl pH 8.3, 1.5 mM MgCl$_2$, 50 mM KCl, 20 μM each dATP, dGTP, dTTP, 1 μM dCTP, 100 μCi [α-$^{32}$P]dCTP, and 5 units of Taq polymerase (Boehringer Mannheim). Reactions conditions were: 5 min, 94° C.; followed by 29 cycles of (1 min, 94° C.; 1 min, 55° C.; 1 min, 72° C.); followed by 5 minutes at 72° C. Unincorporated radioactivity was removed by passing the probe over Sephadex G-50 (Pharmacia).

The radiolabeled 918 bp probe was then used to screen 500,000 plaques from a human dermal fibroblast library made in λgt10 (Sims et al., Proc. Nat. Acad. Sci. USA 86:8946, 1989). Multiple (≧60) positive plaques were identified. Approximately 20 of the positive primary plaques were picked and analyzed by amplification with a combination of primers derived from the clone 7 sequence and primers from the λgt10 vector. The primers used were:

c) CAACCAGTGAGTCATCCTC          (directed toward the 5' end of the mRNA)    (SEQ ID:NO 11)

d) CAACCATGAAGCATACCATG         (directed toward the 3' end of the mRNA)    (SEQ ID:NO 12)

e) CGAGCTGCTCTATAGACTGCTGGGTAGTCC  (vector primer, left arm)                 (SEQ ID:NO 13)

f) TAACAGAGGTGGCTTATGAGTATTTCTTCC  (vector primer, right arm)                (SEQ ID:NO 14)

Analysis of the sizes of the amplification products generated using primers (d), (e) and (f) revealed that clones designated 11-1 and 16-1 could be expected to contain the remainder of the ITAK coding region (on the C-terminal side), which was not present in clone 7. This conclusion was verified by direct DNA sequencing of the PCR products from these two clones.

DNA sequence analysis of clones from fibroblast cells and from dendritic cells revealed several variant sequences. For example, nucleotide 419 in FIG. 1A (SEQ ID NO: 8) is an "A" in clones derived from dendritic cells (clones 7 and 2) and a "T" in clones derived from fibroblast cells. This nucleotide change is silent, however, the codon results in an Ile in both cases. In addition, for nucleotide 443, a "C" is found in dendritic cell clones 7 and 2; a "T" is found in fibroblast clones 3 and 16. This variant is silent also. A non-silent variant is found at nucleotide 1405; fibroblast cell clones 3, 11, and 16 have an "A" (His codon) whereas dendritic cell clones 2 and 7 have a "G" (Arg codon). Furthermore, clone 16 has a 36 base insertion at nucleotide 1649. This small insertion appears to be an intron that is normally spliced out of the mature mRNA. The source of the other described variant positions is likely to be natural polymorphisms. It is unlikely that these alterations were introduced during cloning as each variant was found in at least two independently derived clones.

Thus, a composite of clones 7 and 11-1 encodes an entire open reading frame of ITAK. FIG. 1. The open reading frame is 979 amino acids in length. The ITAK domain with homology to protein serine/threonine kinases lies in the N-terminal ≈300 amino acids (amino acids ≈50–300). The closest relative is a kinase called nek1 (GenBank accession number S25284). The ITAK domain corresponding to amino acids ≈300–750 has homology to a family of guanine nucleotide exchange factors for the low molecular weight G proteins ran and TC4. The closest relative is called RCC1 (GenBank accession number A26691, Bischoff and Ponstingl, *Nature* 354:80, 1991).

DNA sequencing was performed using dye-terminator chemistry and custom primers on ABI/Perkin Elmer 373 and 377 automatic DNA sequencers.

Example 5

Direct Polymerase Chain Reaction Cloning of ITAK from cDNA Libraries

A cDNA containing the entire coding region for the ITAK polypeptide is amplified from cellular RNA in a form suitable for subcloning into an appropriate vector. RNA from an appropriate cellular source known to express ITAK, for example human dendritic cells, human dermal fibroblasts or KB cells (see Examples 3 and 4), is used as template for first strand cDNA synthesis. Briefly, 1–5 μg of total RNA is mixed with 0.5 μg of oligodT$_{12-18}$ primer in 12 μl final volume and heated to 70° C. for 1 min, then chilled on ice. To the above mixture are added 2 μl 1033 PCR buffer (200 mM Tris-HCl pH 8.4, 500 mM KCl), 2 μl 25 mM MgCl$_2$, 2 μl 10 mM mixed dNTPs (10 mM each dATP, dGTP, dCTP, and dTTP), and 2 μl 0.1 M dithiothreitol, and the reaction is allowed to proceed for 5 min at 42° C. Superscript RTII reverse transcriptase (200 units) (GibcoBRL, Gaithersburg, Md.) is added to the reaction, which proceeds for 50 min at 42° C. and is halted by incubation at 70° C. for 15 min, after which the mixture is held on ice. RNase H (4 units) (GibcoBRL) is added to the reaction and incubated for 20 min at 37° C.

To generate ITAK-encoding cDNA, 2 μl of the first strand cDNA is used as a template in a 50 μl polymerase chain reaction (PCR) containing 25 pmol of each primer, 10 mM Tris-HCl pH 8.3, 1.5 mM MgCl$_2$, 50 mM KCl, 200 μM each of dATP, dGTP, dCTP, and dTTP, and 2.5 units of Taq polymerase (Boehringer Mannheim, Indianapolis, Ind.). Reaction conditions are: 1 cycle of (5 min 94° C.; 1 min 64° C.; 2 min 72° C.); 29 cycles of (1 min 94° C.; 1 min 64° C.; 2 min 72° C.); followed by 5 min at 72° C. Suitable primers would contain the following sequences:

a) 5' primer:  ATGTCGGTGCTGGGCGAG  (SEQ ID:NO 15)

b) 3' primer:  CTAGAGGCTGGGTCTACAG (SEQ ID:NO 16)

In order to clone the ITAK coding segment in a vector suitable for mammalian expression, for example the expression plasmid pDC304 (sfNCAV, Immunex, Seattle, Wash.) or other expression plasmids well known in the art, the isolated PCR product fragment is ligated into a vector that has been cut with a suitable restriction enzyme, for example Not1 in the case of pDC304, and that has had the restriction site subsequently blunt-ended by filling in with T4 DNA polymerase and dNTPs (Sambrook et al., supra). Alternatively, the primers may be synthesized with, for example, Not1 restriction sites on their 5' ends:

a) alt. 5' primer:
ATATGCGGCCGCATGTCGGTGCTGGGCGAG        (SEQ ID:NO 17)

b) alt. 3' primer:
ATATGCGGCCGCCTAGAGGCTGGGTCTACAG       (SEQ ID:NO 18)

In this instance, the isolated PCR product is digested with Not1 and ligated into the Not1-cut vector without the intermediate end-filling step.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method of screening for an agent that modulates the kinase activity of an IL-1/TNF-α-activated kinase (ITAK), comprising:

(a) contacting a candidate agent with biologically active ITAK under conditions and for a time sufficient to allow the candidate agent to modulate the kinase activity of said ITAK; and (b) measuring the ability of the candidate agent to modulate the ITAK kinase activity, wherein said IL-1/TNF-α-activated kinase is a protein comprising an amino acid sequence that is at least 80% identical to SEQ ID NO:2.

2. The method of claim 1, further comprising isolating the candidate agent.

* * * * *

UNITED STATES PATENT AND TRADEMARK OFFICE
CERTIFICATE OF CORRECTION

PATENT NO. : 6,913,893 B2
APPLICATION NO. : 10/372736
DATED : July 5, 2005
INVENTOR(S) : Sims et al.

Page 1 of 1

It is certified that error appears in the above-identified patent and that said Letters Patent is hereby corrected as shown below:

Column 1, Line 17: Add a period to the end of the sentence after "(ITAK)".

Column 6, Line 16: Change "interferon-β, interferon-β," to --interferon-β, interferon-γ, --

Column 14, Line 34: Change "IL4" to -- IL-4 --

Column 18, Line 13: Add a closing parenthesis --)-- after "RCC1".

Column 26, Line 37: Add a period after the word "gradient".

Column 27, Line 11: Change "M, = 350 kD." to -- $M_r$ = 350 kD. --

Column 29, Line 41: Change " slected" to -- selected --

Column 32, Line 1: Change "KCl" to -- KC1 --

Column 33, Line 26: Change "1033 PCR" to -- 10X PCR --

Signed and Sealed this

Thirteenth Day of February, 2007

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 2940
<212> TYPE: DNA
<213> ORGANISM: Homo sapiens
<220> FEATURE:
<221> NAME/KEY: CDS
<222> LOCATION: (1)..(2940)

<400> SEQUENCE: 1 atg tcg gtg ctg ggc gag tac gag cga cac tgc gat tcc atc aac tcg      48
Met Ser Val Leu Gly Glu Tyr Glu Arg His Cys Asp Ser Ile Asn Ser
 1               5                  10                  15 gac ttt ggg agc gag tcc ggg ggt tgc ggg gac tcg agt ccg ggg cct      96
Asp Phe Gly Ser Glu Ser Gly Gly Cys Gly Asp Ser Ser Pro Gly Pro
            20                  25                  30 agc gcc agt cag ggg ccg cga gcc ggc ggc ggc gcg gcg gag cag gag     144
Ser Ala Ser Gln Gly Pro Arg Ala Gly Gly Gly Ala Ala Glu Gln Glu
        35                  40                  45
```

```
                                                    -continued gaa ctg cac tac atc ccc atc cgc gtc ctg ggc cgc ggc gcc ttc ggg       192
Glu Leu His Tyr Ile Pro Ile Arg Val Leu Gly Arg Gly Ala Phe Gly
     50                  55                  60 gaa gcc acg ctg tac cgc cgc acc gag gat gac tca ctg gtt gtg tgg       240
Glu Ala Thr Leu Tyr Arg Arg Thr Glu Asp Asp Ser Leu Val Val Trp
 65              70                  75                  80 aag gaa gtc gat ttg acc cgg ctg tct gag aag gaa cgt cgt gat gcc       288
Lys Glu Val Asp Leu Thr Arg Leu Ser Glu Lys Glu Arg Arg Asp Ala
                 85                  90                  95 ttg aat gag ata gtt att ctg gca ctg ctg cag cac gac aac att att       336
Leu Asn Glu Ile Val Ile Leu Ala Leu Leu Gln His Asp Asn Ile Ile
                100                 105                 110 gcc tac tac aat cac ttc atg gac aat acc acg ctg ctg att gag ctg       384
Ala Tyr Tyr Asn His Phe Met Asp Asn Thr Thr Leu Leu Ile Glu Leu
            115                 120                 125 gaa tat tgt aat gga ggg aac ctg tat gac aaa atc ctt cgt cag aag       432
Glu Tyr Cys Asn Gly Gly Asn Leu Tyr Asp Lys Ile Leu Arg Gln Lys
        130                 135                 140 gac aag ttg ttt gag gaa gag atg gtg gtg tgg tac cta ttt cag att       480
Asp Lys Leu Phe Glu Glu Glu Met Val Val Trp Tyr Leu Phe Gln Ile
145                 150                 155                 160 gtt tca gca gtg agc tgc atc cat aaa gct gga atc ctt cat aga gat       528
Val Ser Ala Val Ser Cys Ile His Lys Ala Gly Ile Leu His Arg Asp
                165                 170                 175 ata aag aca tta aat att ttt ctg acc aag gca aac ctg ata aaa ctt       576
Ile Lys Thr Leu Asn Ile Phe Leu Thr Lys Ala Asn Leu Ile Lys Leu
                180                 185                 190 gga gat tat ggc cta gca aag aaa ctt aat tct gag tat tcc atg gct       624
Gly Asp Tyr Gly Leu Ala Lys Lys Leu Asn Ser Glu Tyr Ser Met Ala
            195                 200                 205 gag acg ctt gtg gga acc cca tat tac atg tct cca gag ctc tgt caa       672
Glu Thr Leu Val Gly Thr Pro Tyr Tyr Met Ser Pro Glu Leu Cys Gln
        210                 215                 220 gga gta aag tac aat ttc aag tct gat atc tgg gca gtt ggc tgc gtc       720
Gly Val Lys Tyr Asn Phe Lys Ser Asp Ile Trp Ala Val Gly Cys Val
225                 230                 235                 240 att ttt gaa ctg ctt acc tta aag agg acg ttt gat gct aca aac cca       768
Ile Phe Glu Leu Leu Thr Leu Lys Arg Thr Phe Asp Ala Thr Asn Pro
                245                 250                 255 ctt aac ctg tgt gtg aag atc gtg caa gga att cgg gcc atg gaa gtt       816
Leu Asn Leu Cys Val Lys Ile Val Gln Gly Ile Arg Ala Met Glu Val
                260                 265                 270 gac tct agc cag tac tct ttg gaa ttg atc caa atg gtt cat tcg tgc       864
Asp Ser Ser Gln Tyr Ser Leu Glu Leu Ile Gln Met Val His Ser Cys
            275                 280                 285 ctt gac cag gat cct gag cag aga cct act gca gat gaa ctt cta gat       912
Leu Asp Gln Asp Pro Glu Gln Arg Pro Thr Ala Asp Glu Leu Leu Asp
        290                 295                 300 cgc cct ctt ctc agg aaa cgc agg aga gag atg gag gaa aaa gtc act       960
Arg Pro Leu Leu Arg Lys Arg Arg Arg Glu Met Glu Glu Lys Val Thr
305                 310                 315                 320 ctg ctt aat gca cct aca aag aga cca agg tca agc act gtg act gaa      1008
Leu Leu Asn Ala Pro Thr Lys Arg Pro Arg Ser Ser Thr Val Thr Glu
                325                 330                 335 gca ccc att gct gta gta aca tca cga acc agt gaa gtc tat gtt tgg      1056
Ala Pro Ile Ala Val Val Thr Ser Arg Thr Ser Glu Val Tyr Val Trp
                340                 345                 350 ggt ggt gga aaa tcc acc ccc cag aaa ctg gat gtt atc aag agt ggc      1104
Gly Gly Gly Lys Ser Thr Pro Gln Lys Leu Asp Val Ile Lys Ser Gly
            355                 360                 365
```

-continued

```
tgt agt gcc cgg cag gtc tgt gca ggg aat acc cac ttt gct gtg gtc      1152
Cys Ser Ala Arg Gln Val Cys Ala Gly Asn Thr His Phe Ala Val Val
    370                 375                 380 aca gtg gag aag gaa ctg tac act tgg gtg aac atg caa gga ggc act      1200
Thr Val Glu Lys Glu Leu Tyr Thr Trp Val Asn Met Gln Gly Gly Thr
385                 390                 395                 400 aaa ctc cat ggt cag ctg ggc cat gga gac aaa gcc tcc tat cga cag      1248
Lys Leu His Gly Gln Leu Gly His Gly Asp Lys Ala Ser Tyr Arg Gln
                405                 410                 415 cca aag cat gtg gaa aag ttg caa ggc aaa gct atc cat cag gtg tca      1296
Pro Lys His Val Glu Lys Leu Gln Gly Lys Ala Ile His Gln Val Ser
            420                 425                 430 tgt ggt gat gat ttc act gtc tgt gtg act gat gag ggt cag ctc tat      1344
Cys Gly Asp Asp Phe Thr Val Cys Val Thr Asp Glu Gly Gln Leu Tyr
        435                 440                 445 gcc ttc gga tca gat tat tat ggc tgc atg ggg gtg gac aaa gtt gct      1392
Ala Phe Gly Ser Asp Tyr Tyr Gly Cys Met Gly Val Asp Lys Val Ala
    450                 455                 460 ggc cct gaa gtg cta gaa ccc atg cag ctg aac ttc ttc ctc agc aat      1440
Gly Pro Glu Val Leu Glu Pro Met Gln Leu Asn Phe Phe Leu Ser Asn
465                 470                 475                 480 cca gtg gag cag gtc tcc tgt gga gat aat cat gtg gtg gtt ctg aca      1488
Pro Val Glu Gln Val Ser Cys Gly Asp Asn His Val Val Val Leu Thr
                485                 490                 495 cga aac aag gaa gtc tat tct tgg ggc tgt ggc gaa tat gga cga ctg      1536
Arg Asn Lys Glu Val Tyr Ser Trp Gly Cys Gly Glu Tyr Gly Arg Leu
            500                 505                 510 ggt ttg gat tca gaa gag gat tat tat aca cca caa aag gtg gat gtt      1584
Gly Leu Asp Ser Glu Glu Asp Tyr Tyr Thr Pro Gln Lys Val Asp Val
        515                 520                 525 ccc aag gcc ttg att att gtt gca gtt caa tgt ggc tgt gat ggg aca      1632
Pro Lys Ala Leu Ile Ile Val Ala Val Gln Cys Gly Cys Asp Gly Thr
    530                 535                 540 ttt ctg ttg acc cag tca ggc aaa gtg ctg gcc tgt gga ctc aat gaa      1680
Phe Leu Leu Thr Gln Ser Gly Lys Val Leu Ala Cys Gly Leu Asn Glu
545                 550                 555                 560 ttc aat aag ctg ggt ctg aat cag tgc atg tcg gga att atc aac cat      1728
Phe Asn Lys Leu Gly Leu Asn Gln Cys Met Ser Gly Ile Ile Asn His
                565                 570                 575 gaa gca tac cat gaa gtt ccc tac aca acg tcc ttt acc ttg gcc aaa      1776
Glu Ala Tyr His Glu Val Pro Tyr Thr Thr Ser Phe Thr Leu Ala Lys
            580                 585                 590 cag ttg tcc ttt tat aag atc cgt acc att gcc cca ggc aag act cac      1824
Gln Leu Ser Phe Tyr Lys Ile Arg Thr Ile Ala Pro Gly Lys Thr His
        595                 600                 605 aca gct gct att gat gag cga ggc cgg ctg ctg acc ttt ggc tgc aac      1872
Thr Ala Ala Ile Asp Glu Arg Gly Arg Leu Leu Thr Phe Gly Cys Asn
    610                 615                 620 aag tgt ggg cag ctg ggc gtt ggg aac tac aag aag cgt ctg gga atc      1920
Lys Cys Gly Gln Leu Gly Val Gly Asn Tyr Lys Lys Arg Leu Gly Ile
625                 630                 635                 640 aac ctg ttg ggg gga ccc ctt ggt ggg aag caa gtg atc agg gtc tcc      1968
Asn Leu Leu Gly Gly Pro Leu Gly Gly Lys Gln Val Ile Arg Val Ser
                645                 650                 655 tgc ggt gat gag ttt acc att gct gcc act gat gat aat cac att ttt      2016
Cys Gly Asp Glu Phe Thr Ile Ala Ala Thr Asp Asp Asn His Ile Phe
            660                 665                 670 gcc tgg ggc aat ggt ggt aat ggc cgc ctg gca atg acc ccc aca gag      2064
Ala Trp Gly Asn Gly Gly Asn Gly Arg Leu Ala Met Thr Pro Thr Glu
```

```
                                    -continued
              675              680              685
aga cca cat ggc tct gat atc tgt acc tca tgg cct cgg cct att ttt   2112
Arg Pro His Gly Ser Asp Ile Cys Thr Ser Trp Pro Arg Pro Ile Phe
        690              695              700 gga tct ctg cat cat gtc ccg gac ctg tct tgc cgt gga tgg cat acc   2160
Gly Ser Leu His His Val Pro Asp Leu Ser Cys Arg Gly Trp His Thr
705              710              715              720 att ctc atc gtt gag aaa gta ttg aat tct aag acc atc cgt tcc aat   2208
Ile Leu Ile Val Glu Lys Val Leu Asn Ser Lys Thr Ile Arg Ser Asn
                725              730              735 agc agt ggc tta tcc att gga act gtg ttt cag agc tct agc ccg gga   2256
Ser Ser Gly Leu Ser Ile Gly Thr Val Phe Gln Ser Ser Ser Pro Gly
            740              745              750 gga ggc ggc ggg ggc ggc ggt ggt gaa gaa gag gac agt cag cag gaa   2304
Gly Gly Gly Gly Gly Gly Gly Gly Glu Glu Glu Asp Ser Gln Gln Glu
        755              760              765 tct gaa act cct gac cca agt gga ggc ttc cga gga aca atg gaa gca   2352
Ser Glu Thr Pro Asp Pro Ser Gly Gly Phe Arg Gly Thr Met Glu Ala
    770              775              780 gac cga gga atg gaa ggt tta atc agt ccc aca gag gcc atg ggg aac   2400
Asp Arg Gly Met Glu Gly Leu Ile Ser Pro Thr Glu Ala Met Gly Asn
785              790              795              800 agt aat ggg gcc agc agc tcc tgt cct ggc tgg ctt cga aag gag ctg   2448
Ser Asn Gly Ala Ser Ser Ser Cys Pro Gly Trp Leu Arg Lys Glu Leu
                805              810              815 gaa aat gca gaa ttt atc ccc atg cct gac agc cca tct cct ctc agt   2496
Glu Asn Ala Glu Phe Ile Pro Met Pro Asp Ser Pro Ser Pro Leu Ser
            820              825              830 gca gcg ttt tca gaa tct gag aaa gat acc ctg ccc tat gaa gag ctg   2544
Ala Ala Phe Ser Glu Ser Glu Lys Asp Thr Leu Pro Tyr Glu Glu Leu
        835              840              845 caa gga ctc aaa gtg gcc tct gaa gct cct ttg gaa cac aaa ccc caa   2592
Gln Gly Leu Lys Val Ala Ser Glu Ala Pro Leu Glu His Lys Pro Gln
    850              855              860 gta gaa gcc tcg tca cct cgg ctg aat cct gca gta acc tgt gct ggg   2640
Val Glu Ala Ser Ser Pro Arg Leu Asn Pro Ala Val Thr Cys Ala Gly
865              870              875              880 aag gga aca cca ctg act cct cct gcg tgt gcg tgc agc tct ctg cag   2688
Lys Gly Thr Pro Leu Thr Pro Pro Ala Cys Ala Cys Ser Ser Leu Gln
                885              890              895 gtg gag gtt gag aga ttg cag ggt ctg gtg tta aag tgt ctg gct gaa   2736
Val Glu Val Glu Arg Leu Gln Gly Leu Val Leu Lys Cys Leu Ala Glu
            900              905              910 caa cag aag cta cag caa gaa aac ctc cag att ttt acc caa ctg cag   2784
Gln Gln Lys Leu Gln Gln Glu Asn Leu Gln Ile Phe Thr Gln Leu Gln
        915              920              925 aag ttg aac aag aaa tta gaa gga ggg cag cag gtg ggg atg cat tcc   2832
Lys Leu Asn Lys Lys Leu Glu Gly Gly Gln Gln Val Gly Met His Ser
    930              935              940 aaa gga act cag aca gca aag gaa gag atg gaa atg gat cca aag cct   2880
Lys Gly Thr Gln Thr Ala Lys Glu Glu Met Glu Met Asp Pro Lys Pro
945              950              955              960 gac tta gat tca gat tcc tgg tgc ctc ctg gga aca gac tcc tgt aga   2928
Asp Leu Asp Ser Asp Ser Trp Cys Leu Leu Gly Thr Asp Ser Cys Arg
                965              970              975 ccc agc ctc tag                                                   2940
Pro Ser Leu
        980
```

<210> SEQ ID NO 2
<211> LENGTH: 979
<212> TYPE: PRT
<213> ORGANISM: Homo sapiens

<400> SEQUENCE: 2

Met Ser Val Leu Gly Glu Tyr Glu Arg His Cys Asp Ser Ile Asn Ser
1               5                   10                  15

Asp Phe Gly Ser Glu Ser Gly Gly Cys Gly Asp Ser Ser Pro Gly Pro
            20                  25                  30

Ser Ala Ser Gln Gly Pro Arg Ala Gly Gly Ala Ala Glu Gln Glu
        35                  40                  45

Glu Leu His Tyr Ile Pro Ile Arg Val Leu Gly Arg Gly Ala Phe Gly
    50                  55                  60

Glu Ala Thr Leu Tyr Arg Arg Thr Glu Asp Asp Ser Leu Val Val Trp
65                  70                  75                  80

Lys Glu Val Asp Leu Thr Arg Leu Ser Glu Lys Glu Arg Arg Asp Ala
                85                  90                  95

Leu Asn Glu Ile Val Ile Leu Ala Leu Leu Gln His Asp Asn Ile Ile
            100                 105                 110

Ala Tyr Tyr Asn His Phe Met Asp Asn Thr Thr Leu Leu Ile Glu Leu
        115                 120                 125

Glu Tyr Cys Asn Gly Gly Asn Leu Tyr Asp Lys Ile Leu Arg Gln Lys
    130                 135                 140

Asp Lys Leu Phe Glu Glu Glu Met Val Val Trp Tyr Leu Phe Gln Ile
145                 150                 155                 160

Val Ser Ala Val Ser Cys Ile His Lys Ala Gly Ile Leu His Arg Asp
                165                 170                 175

Ile Lys Thr Leu Asn Ile Phe Leu Thr Lys Ala Asn Leu Ile Lys Leu
            180                 185                 190

Gly Asp Tyr Gly Leu Ala Lys Lys Leu Asn Ser Glu Tyr Ser Met Ala
        195                 200                 205

Glu Thr Leu Val Gly Thr Pro Tyr Tyr Met Ser Pro Glu Leu Cys Gln
    210                 215                 220

Gly Val Lys Tyr Asn Phe Lys Ser Asp Ile Trp Ala Val Gly Cys Val
225                 230                 235                 240

Ile Phe Glu Leu Leu Thr Leu Lys Arg Thr Phe Asp Ala Thr Asn Pro
                245                 250                 255

Leu Asn Leu Cys Val Lys Ile Val Gln Gly Ile Arg Ala Met Glu Val
            260                 265                 270

Asp Ser Ser Gln Tyr Ser Leu Glu Leu Ile Gln Met Val His Ser Cys
        275                 280                 285

Leu Asp Gln Asp Pro Glu Gln Arg Pro Thr Ala Asp Glu Leu Leu Asp
    290                 295                 300

Arg Pro Leu Leu Arg Lys Arg Arg Glu Met Glu Glu Lys Val Thr
305                 310                 315                 320

Leu Leu Asn Ala Pro Thr Lys Arg Pro Arg Ser Ser Thr Val Thr Glu
                325                 330                 335

Ala Pro Ile Ala Val Val Thr Ser Arg Thr Ser Glu Val Tyr Val Trp
            340                 345                 350

Gly Gly Gly Lys Ser Thr Pro Gln Lys Leu Asp Val Ile Lys Ser Gly
        355                 360                 365

Cys Ser Ala Arg Gln Val Cys Ala Gly Asn Thr His Phe Ala Val Val
    370                 375                 380

-continued

```
Thr Val Glu Lys Glu Leu Tyr Thr Trp Val Asn Met Gln Gly Gly Thr
385                 390                 395                 400

Lys Leu His Gly Gln Leu Gly His Gly Asp Lys Ala Ser Tyr Arg Gln
            405                 410                 415

Pro Lys His Val Glu Lys Leu Gln Gly Lys Ala Ile His Gln Val Ser
            420                 425                 430

Cys Gly Asp Asp Phe Thr Val Cys Val Thr Asp Glu Gly Gln Leu Tyr
            435                 440                 445

Ala Phe Gly Ser Asp Tyr Tyr Gly Cys Met Gly Val Asp Lys Val Ala
        450                 455                 460

Gly Pro Glu Val Leu Glu Pro Met Gln Leu Asn Phe Phe Leu Ser Asn
465                 470                 475                 480

Pro Val Glu Gln Val Ser Cys Gly Asp Asn His Val Val Leu Thr
            485                 490                 495

Arg Asn Lys Glu Val Tyr Ser Trp Gly Cys Gly Glu Tyr Gly Arg Leu
            500                 505                 510

Gly Leu Asp Ser Glu Glu Asp Tyr Tyr Thr Pro Gln Lys Val Asp Val
            515                 520                 525

Pro Lys Ala Leu Ile Ile Val Ala Val Gln Cys Gly Cys Asp Gly Thr
            530                 535                 540

Phe Leu Leu Thr Gln Ser Gly Lys Val Leu Ala Cys Gly Leu Asn Glu
545                 550                 555                 560

Phe Asn Lys Leu Gly Leu Asn Gln Cys Met Ser Gly Ile Ile Asn His
            565                 570                 575

Glu Ala Tyr His Glu Val Pro Tyr Thr Thr Ser Phe Thr Leu Ala Lys
            580                 585                 590

Gln Leu Ser Phe Tyr Lys Ile Arg Thr Ile Ala Pro Gly Lys Thr His
            595                 600                 605

Thr Ala Ala Ile Asp Glu Arg Gly Arg Leu Leu Thr Phe Gly Cys Asn
            610                 615                 620

Lys Cys Gly Gln Leu Gly Val Gly Asn Tyr Lys Lys Arg Leu Gly Ile
625                 630                 635                 640

Asn Leu Leu Gly Gly Pro Leu Gly Gly Lys Gln Val Ile Arg Val Ser
            645                 650                 655

Cys Gly Asp Glu Phe Thr Ile Ala Ala Thr Asp Asp Asn His Ile Phe
            660                 665                 670

Ala Trp Gly Asn Gly Gly Asn Gly Arg Leu Ala Met Thr Pro Thr Glu
            675                 680                 685

Arg Pro His Gly Ser Asp Ile Cys Thr Ser Trp Pro Arg Pro Ile Phe
            690                 695                 700

Gly Ser Leu His His Val Pro Asp Leu Ser Cys Arg Gly Trp His Thr
705                 710                 715                 720

Ile Leu Ile Val Glu Lys Val Leu Asn Ser Lys Thr Ile Arg Ser Asn
            725                 730                 735

Ser Ser Gly Leu Ser Ile Gly Thr Val Phe Gln Ser Ser Pro Gly
            740                 745                 750

Gly Gly Gly Gly Gly Gly Glu Glu Asp Ser Gln Gln Glu
            755                 760                 765

Ser Glu Thr Pro Asp Pro Ser Gly Gly Phe Arg Gly Thr Met Glu Ala
            770                 775                 780

Asp Arg Gly Met Glu Gly Leu Ile Ser Pro Thr Glu Ala Met Gly Asn
785                 790                 795                 800

Ser Asn Gly Ala Ser Ser Ser Cys Pro Gly Trp Leu Arg Lys Glu Leu
```

-continued

```
                    805                 810                 815
Glu Asn Ala Glu Phe Ile Pro Met Pro Asp Ser Pro Ser Pro Leu Ser
            820                 825                 830
Ala Ala Phe Ser Glu Ser Glu Lys Asp Thr Leu Pro Tyr Glu Glu Leu
            835                 840                 845
Gln Gly Leu Lys Val Ala Ser Glu Ala Pro Leu Glu His Lys Pro Gln
        850                 855                 860
Val Glu Ala Ser Ser Pro Arg Leu Asn Pro Ala Val Thr Cys Ala Gly
865                 870                 875                 880
Lys Gly Thr Pro Leu Thr Pro Pro Ala Cys Ala Cys Ser Ser Leu Gln
                885                 890                 895
Val Glu Val Glu Arg Leu Gln Gly Leu Val Leu Lys Cys Leu Ala Glu
                900                 905                 910
Gln Gln Lys Leu Gln Gln Glu Asn Leu Gln Ile Phe Thr Gln Leu Gln
            915                 920                 925
Lys Leu Asn Lys Lys Leu Glu Gly Gly Gln Gln Val Gly Met His Ser
        930                 935                 940
Lys Gly Thr Gln Thr Ala Lys Glu Glu Met Glu Met Asp Pro Lys Pro
945                 950                 955                 960
Asp Leu Asp Ser Asp Ser Trp Cys Leu Leu Gly Thr Asp Ser Cys Arg
                965                 970                 975
Pro Ser Leu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: synthetic
      peptide substrate

<400> SEQUENCE: 3

Arg Arg Arg His Leu Pro Pro Leu Leu Leu Gln Ser Trp Met His Gln
  1               5                  10                  15
Pro His Gln

<210> SEQ ID NO 4
<211> LENGTH: 10
<212> TYPE: PRT
<213> ORGANISM: Oryctolagus cuniculus

<400> SEQUENCE: 4

Gly Ala Phe Gly Glu Ala Thr Leu Tyr Arg
  1               5                  10

<210> SEQ ID NO 5
<211> LENGTH: 9
<212> TYPE: PRT
<213> ORGANISM: Oryctolagus cuniculus

<400> SEQUENCE: 5

Val Thr Leu Leu Asn Ala Pro Thr Lys
  1               5

<210> SEQ ID NO 6
<211> LENGTH: 15
<212> TYPE: PRT
<213> ORGANISM: Oryctolagus cuniculus

<400> SEQUENCE: 6
```

Ser Ser Thr Val Thr Glu Ala Pro Ile Ala Val Val Thr Ser Arg
 1               5                  10                  15

<210> SEQ ID NO 7
<211> LENGTH: 19
<212> TYPE: PRT
<213> ORGANISM: Oryctolagus cuniculus

<400> SEQUENCE: 7

Leu Gly Leu Asp Ser Glu Glu Asp Tyr Tyr Thr Pro Gln Lys Val Asp
 1               5                  10                  15

Val Pro Lys

<210> SEQ ID NO 8
<211> LENGTH: 3264
<212> TYPE: DNA
<213> ORGANISM: Homo sapiens

<400> SEQUENCE: 8

| | | | | |
|---|---|---|---|---|
| tcttcgcggg | gttgctgggc | tgacggatcc | gcgggccggc | atctgaagcg agcgggacgc | 60 |
| agcgcggcca | gggcctccgg | gcatacgcag | gctggtcccc | aaggcccgcg gccgccgcca | 120 |
| tgtcggtgct | gggcgagtac | gagcgacact | gcgattccat | caactcggac tttgggagcg | 180 |
| agtccggggg | ttgcggggac | tcgagtccgg | ggcctagcgc | cagtcagggg ccgcgagccg | 240 |
| gcggcggcgc | ggcggagcag | gaggaactgc | actacatccc | catccgcgtc ctgggccgcg | 300 |
| gcgccttcgg | ggaagccacg | ctgtaccgcc | gcaccgagga | tgactcactg gttgtgtgga | 360 |
| aggaagtcga | tttgacccgg | ctgtctgaga | aggaacgtcg | tgatgccttg aatgagatag | 420 |
| ttattctggc | actgctgcag | cacgacaaca | ttattgccta | ctacaatcac ttcatggaca | 480 |
| ataccacgct | gctgattgag | ctggaatatt | gtaatggagg | gaacctgtat gacaaaatcc | 540 |
| ttcgtcagaa | ggacaagttg | tttgaggaag | agatggtggt | gtggtaccta tttcagattg | 600 |
| tttcagcagt | gagctgcatc | cataaagctg | gaatccttca | tagagatata aagacattaa | 660 |
| atattttttct | gaccaaggca | aacctgataa | aacttggaga | ttatggccta gcaaagaaac | 720 |
| ttaattctga | gtattccatg | gctgagacgc | ttgtgggaac | cccatattac atgtctccag | 780 |
| agctctgtca | aggagtaaag | tacaatttca | gtctgatat | ctgggcagtt ggctgcgtca | 840 |
| ttttttgaact | gcttaccttta | aagaggacgt | ttgatgctac | aaacccactt aacctgtgtg | 900 |
| tgaagatcgt | gcaaggaatt | cgggccatgg | aagttgactc | tagccagtac tctttggaat | 960 |
| tgatccaaat | ggttcattcg | tgccttgacc | aggatcctga | gcagagacct actgcagatg | 1020 |
| aacttctaga | tcgccctctt | ctcaggaaac | gcaggagaga | gatggaggaa aaagtcactc | 1080 |
| tgcttaatgc | acctacaaag | agaccaaggt | caagcactgt | gactgaagca cccattgctg | 1140 |
| tagtaacatc | acgaaccagt | gaagtctatg | tttggggtgg | tggaaaatcc accccccaga | 1200 |
| aactggatgt | tatcaagagt | ggctgtagtg | cccggcaggt | ctgtgcaggg aatacccact | 1260 |
| ttgctgtggt | cacagtggag | aaggaactgt | acacttgggt | gaacatgcaa ggaggcacta | 1320 |
| aactccatgg | tcagctgggc | catggagaca | agcctcctta | tcgacagcca aagcatgtgg | 1380 |
| aaaagttgca | aggcaaagct | atccatcagg | tgtcatgtgg | tgatgatttc actgtctgtg | 1440 |
| tgactgatga | gggtcagctc | tatgccttcg | gatcagatta | ttatgctgc atgggggtgg | 1500 |
| acaaagttgc | tggccctgaa | gtgctagaac | ccatgcagct | gaacttcttc ctcagcaatc | 1560 |
| cagtggagca | ggtctcctgt | ggagataatc | atgtggtggt | tctgacacga aacaaggaag | 1620 |

-continued

```
tctattcttg gggctgtggc gaatatggac gactgggttt ggattcagaa gaggattatt      1680
atacaccaca aaaggtggat gttcccaagg ccttgattat tgttgcagtt caatgtggct      1740
gtgatgggac atttctgttg acccagtcag gcaaagtgct ggcctgtgga ctcaatgaat      1800
tcaataagct gggtctgaat cagtgcatgt cgggaattat caaccatgaa gcataccatg      1860
aagttcccta cacaacgtcc tttaccttgg ccaaacagtt gtccttttat aagatccgta      1920
ccattgcccc aggcaagact cacacagctg ctattgatga gcgaggccgg ctgctgacct      1980
ttggctgcaa caagtgtggg cagctgggcg ttgggaacta caagaagcgt ctgggaatca      2040
acctgttggg gggacccctt ggtgggaagc aagtgatcag ggtctcctgc ggtgatgagt      2100
ttaccattgc tgccactgat gataatcaca ttttgcctg gggcaatggt ggtaatggcc       2160
gcctggcaat gacccccaca gagagaccac atggctctga tatctgtacc tcatggcctc      2220
ggcctatttt tggatctctg catcatgtcc cggacctgtc ttgccgtgga tggcatacca      2280
ttctcatcgt tgagaaagta ttgaattcta agaccatccg ttccaatagc agtggcttat      2340
ccattggaac tgtgtttcag agctctagcc cgggaggagg cggcggggc ggcggtggtg       2400
aagaagagga cagtcagcag gaatctgaaa ctcctgaccc aagtggaggc ttccgaggaa      2460
caatggaagc agaccgagga atggaaggtt taatcagtcc cacagaggcc atgggaaca      2520
gtaatggggc cagcagctcc tgtcctggct ggcttcgaaa ggagctggaa aatgcagaat      2580
ttatccccat gcctgacagc ccatctcctc tcagtgcagc gttttcagaa tctgagaaag      2640
ataccctgcc ctatgaagag ctgcaaggac tcaaagtggc ctctgaagct cctttggaac      2700
acaaacccca agtagaagcc tcgtcacctc ggctgaatcc tgcagtaacc tgtgctggga      2760
agggaacacc actgactcct cctgcgtgtg cgtgcagctc tctgcaggtg gaggttgaga      2820
gattgcaggg tctggtgtta aagtgtctgg ctgaacaaca gaagctacag caagaaaacc      2880
tccagatttt tacccaactg cagaagttga acaagaaatt agaaggaggg cagcaggtgg      2940
ggatgcattc caaggaact cagacagcaa aggaagagat ggaaatggat ccaaagcctg       3000
acttagattc agattcctgg tgcctcctgg gaacagactc ctgtagaccc agcctctagt      3060
ctcctgagcc tatagagccc ccaggagact gggacccaaa gaacttcaca gcacacttac      3120
cgaatgcaga gagcagcttt cctggctttg ttcacttgca gaaaaggagc gcaaggcaga      3180
ggctctgaag cactttcctt gtacatttgg agagtggcat tgccttttag ataggattag      3240
gccggatatt ttgcttttta ccct                                              3264
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 9
ccatggctga gacgcttg       18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 10
gtcgtccata ttcgccacag                                        20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 11
caaccagtga gtcatcctc                                         19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 12
caaccatgaa gcataccatg                                        20

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 13
cgagctgctc tatagactgc tgggtagtcc                             30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 14
taacagaggt ggcttatgag tatttcttcc                             30

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 15
atgtcggtgc tgggcgag                                          18

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 16

-continued

```
ctagaggctg ggtctacag                                                    19

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 17
atatgcggcc gcatgtcggt gctgggcgag                                        30

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide primer

<400> SEQUENCE: 18
atatgcggcc gcctagaggc tgggtctaca g                                      31
```